United States Patent
Kodam et al.

(10) Patent No.: US 11,408,871 B2
(45) Date of Patent: Aug. 9, 2022

(54) INTERNET-OF-THINGS SMELL SENSOR DEVICES AND SERVICES

(71) Applicant: DISH Network L.L.C., Englewood, CO (US)

(72) Inventors: Sheshank Kodam, Aurora, CO (US); Nicholas Newell, Centennial, CO (US)

(73) Assignee: DISH Network L.L.C., Englewood, CO (US)

(*) Notice: Subject to any disclaimer, the term of this patent is extended or adjusted under 35 U.S.C. 154(b) by 780 days.

(21) Appl. No.: 16/380,592

(22) Filed: Apr. 10, 2019

(65) Prior Publication Data

US 2020/0213146 A1  Jul. 2, 2020

Related U.S. Application Data

(60) Provisional application No. 62/787,049, filed on Dec. 31, 2018.

(51) Int. Cl.
| | |
|---|---|
| *G01N 33/00* | (2006.01) |
| *H04L 12/28* | (2006.01) |
| *G06F 21/32* | (2013.01) |
| *G01S 15/06* | (2006.01) |

(52) U.S. Cl.
CPC ..... *G01N 33/0031* (2013.01); *G01N 33/0057* (2013.01); *G01S 15/06* (2013.01); *G06F 21/32* (2013.01); *H04L 12/2829* (2013.01)

(58) Field of Classification Search
CPC ............ G01N 33/0031; G01N 33/0057; G01S 15/06; H04L 12/2829; H04L 12/2827; G06F 21/32
See application file for complete search history.

(56) References Cited

U.S. PATENT DOCUMENTS

| | | | | |
|---|---|---|---|---|
| 4,638,443 A | * | 1/1987 | Kaneyasu | G01N 33/0031 340/634 |
| 6,703,241 B1 | * | 3/2004 | Sunshine | G01N 33/0006 436/2 |
| 9,945,573 B2 | * | 4/2018 | Balkhair | F24F 11/62 |

* cited by examiner

*Primary Examiner* — Benjamin R Schmitt
(74) *Attorney, Agent, or Firm* — Kilpatrick Townsend & Stockton LLP

(57) ABSTRACT

Various techniques are described herein for using smell sensor-based Internet-of-Things (IoT) devices to detect and identify individual users based a unique scent or smell print. Interconnected networks of such devices may be used in collaboration, along with other devices such as IoT devices and home monitoring system devices, to track user movements and activities. Such smell sensor device also may be used to detect weapons, explosives, narcotics, and other prohibited items that may be concealed and/or not detectable using security cameras. The data received from the smell sensors and smell-based IoT devices may be used, alone or in combination with other security sensors and systems, to perform safety and security screening within homes, airports or other secure areas, or within any public indoor or outdoor location.

20 Claims, 12 Drawing Sheets

| Device ID | Person ID | Smell Print | 3D Model | Steps | Speed | Location | Posture |
|---|---|---|---|---|---|---|---|
| 1234 | 3456 | 1010001 | 10010101 | 400 | 1 m/hr | (39, 40) | Sleeping |

FIG. 7

INTERNET-OF-THINGS SMELL SENSOR DEVICES AND SERVICES

CROSS-REFERENCE TO RELATED APPLICATIONS

The present application is a non-provisional of and claims priority to U.S. Provisional Patent Application No. 62/787,049, filed Dec. 31, 2018, entitled "INTERNET-OF-THINGS SMELL SENSOR DEVICES AND SERVICES." The entire contents of provisional application No. 62/787,049 is incorporated herein by reference for all purposes.

TECHNICAL FIELD

The present disclosure relates to the use of Internet-of-Things (IoT) devices incorporating smell sensors and components, as well as collaborative networks of such IoT devices, to perform personal tracking and monitoring, as well as security screening and threat detection for individuals and at locations.

BACKGROUND

The applications and uses for personal activity monitoring and user tracking technology are expanding rapidly across many different fields and industries. From personal tracking applications used for fitness and medical purposes, to user activity tracking at retail locations for marketing and product placement, to security screening and threat detection at airports and other secure locations, there are many advantages to robust and accurate user tracking and monitoring systems.

Conventional techniques for performing user tracking and monitoring often include wearable devices, such as fitness trackers, smart watches, and other wearable health monitoring devices. However, users often dislike wearable health devices because they may be uncomfortable, time-consuming to charge, unattractive, irritating to the skin, and/or expensive to purchase. Other user monitoring and security systems may involve the use of cameras, infrared sensors, facial recognition technology, and the like, to identify particular users and track user movements and to detect possible threats. However, using camera systems to identify users and remotely track user movements may be considered an invasion of privacy because such systems captures too much personal information. Additionally, camera systems and facial recognition technology may be defeated by user disguises or camera blind-spots, and such systems may not be able to detect concealed items such as weapons that are worn under a layer of clothes or hidden in a bag or container.

SUMMARY

Aspects described herein provide various techniques (e.g., methods, systems, devices, computer-readable media storing computer-executable instructions used to perform computing functions, etc.) using smell sensor-based Internet-of-Things (IoT) devices to detect and identify individual users based a unique scent or smell print. Additionally, interconnected networks of such devices may be used in collaboration, along with other devices (e.g., IoT devices, home monitoring devices, etc.) to track user movements and activities. Further, such smell sensor device may be used to detect weapons, explosives, narcotics, and other prohibited items that may be concealed and/or not detectable using security cameras. Thus, the data received from the smell sensors and smell-based IoT devices may be used, alone or in combination with other security sensors and systems, to perform safety and security screening within homes, airports or other secure areas, or within any public indoor or outdoor location.

Accordingly, certain aspects described here relate to network devices incorporating smell sensors. Such devices may include specialized hardware and/or software components configured to detect airborne odors and scents, and then analyze the smell data to identify particular individuals, objects, or substances. As noted above, the devices may be smell sensor IoT devices, with wireless network interfaces configured to communicate with other similar IoT devices as well as other network-based nodes (e.g., television receivers, modems, routers, smartphones, etc.). In some cases, the smell sensor IoT devices may include memory and software-based components capable of storing a catalog of known unique smells, and then comparing current smells or any newly-detected smells to the catalog in order to identify persons and objects. Additionally, in some embodiments, smell sensor IoT devices may include additional sensors including depth sensors (e.g., infrared sensors, ultrasonic sensors, etc.) configured to detect object presence, distance, shape, and movement. The combination of the smell sensors and depth sensors may allow the device to identify individuals and objects with higher confidence, and also to track the movement and activity of multiple distinct individuals. In some embodiments, smell sensor IoT devices also may include a global positioning system (GPS) receiver or other locational sensor capable of determining the device location, which may be used in collaboration with other device to detect object size and movement, and to "handoff" moving objects to other smell sensor IoT devices within the device network.

Additional aspects described herein relate to coordination and collaboration between multiple smell sensor IoT devices to perform person or object identification, analysis, and tracking. For example, a network of smell sensor IoT devices may communicate location data and data relating to a particular target object (e.g., target location, size, movement, and smell properties). Based on communications between multiple smell sensor IoT devices, a 3D object profile may be generated, and a particular individual or object may be tracked and monitored by a plurality of IoT devices as it moves within an indoor or outdoor location. In such embodiments, smell sensor IoT devices may transmit RF handoff messages to nearby devices, including device identifier data, location data, object identification data and object information, timestamp data, and the like.

Still further aspects described herein relate to using individual smell sensor devices and/or networks of such devices to detect particular objects and substances, such as weapons, explosives, and other dangerous materials. Such objects and substances may have unique smell characteristics that may be detected by smell sensor devices. In response to detecting a dangerous or prohibited object or substance, the smell sensor device may take various actions depending on its location, network of nearby devices, nearby users, and the object/substance detected, including broadcasting alerts and performing functions on other connected devices (e.g., activating alarms, locking doors and windows, etc.).

BRIEF DESCRIPTION OF THE DRAWINGS

The present invention is described in conjunction with the appended figures:

FIG. 7 is example data entry associated with a person tracking/monitoring process executing using a smell sensor device, in accordance with one or more embodiments of the disclosure.

Figure 1:
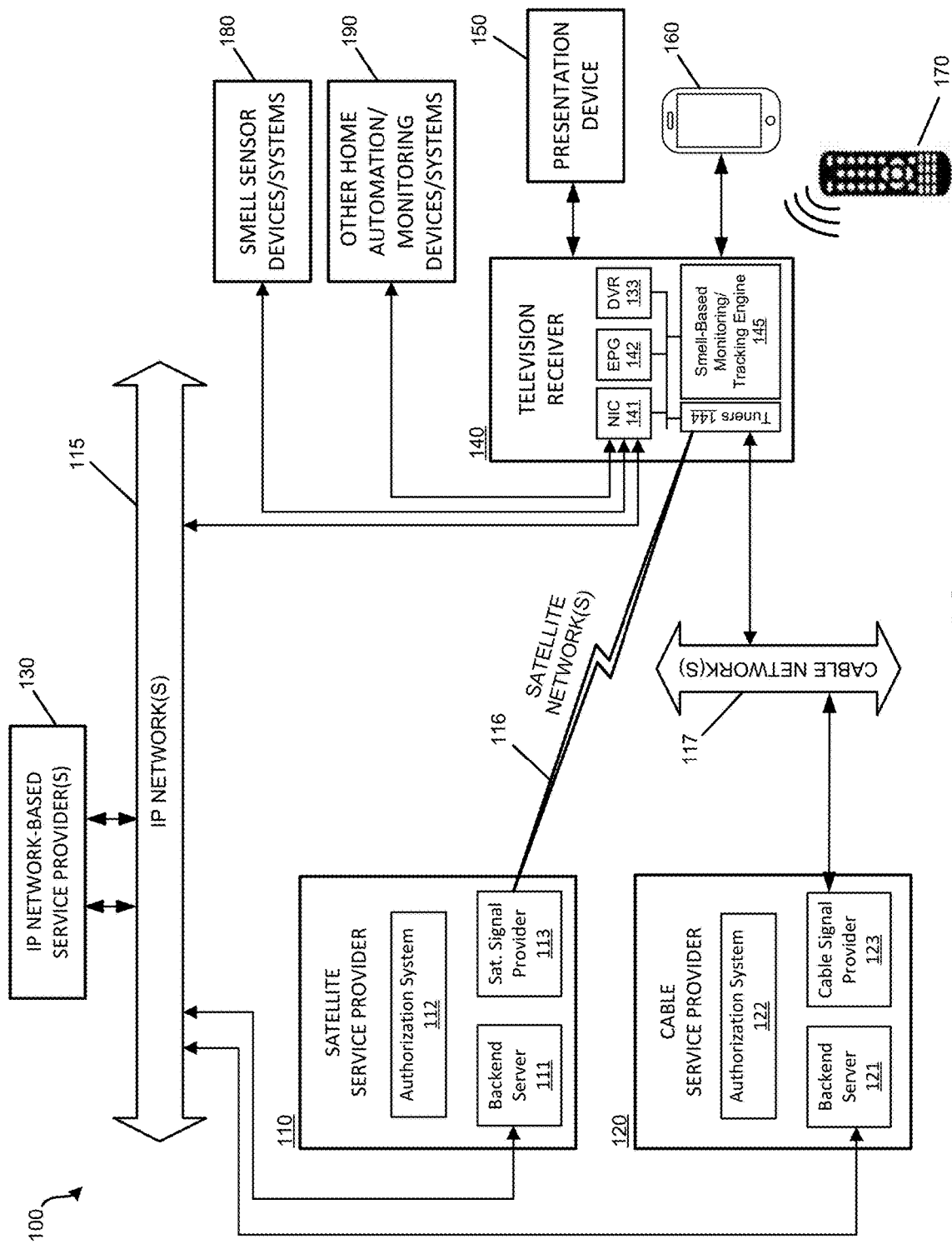
FIG. 1 is a block diagram illustrating a video resource delivery and output system, in accordance with one or more embodiments of the disclosure.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION

In the following description, for the purposes of explanation, specific details are set forth in order to provide a thorough understanding of various implementations and examples. It will be apparent, however, that various implementations may be practiced without these specific details. For example, circuits, systems, algorithms, structures, techniques, networks, processes, and other components may be shown as components in block diagram form in order not to obscure the implementations in unnecessary detail. The figures and description are not intended to be restrictive.

Some examples, such as those disclosed with respect to the figures in this disclosure, may be described as a process which is depicted as a flowchart, a flow diagram, a data flow diagram, a structure diagram, a sequence diagram, or a block diagram. Although a sequence diagram or a flowchart may describe the operations as a sequential process, many of the operations may be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination may correspond to a return of the function to the calling function or the main function.

The processes depicted herein, such as those described with reference to the figures in this disclosure, may be implemented in software (e.g., code, instructions, program) executed by one or more processing units (e.g., processors cores), hardware, or combinations thereof. The software may be stored in a memory (e.g., on a memory device, on a non-transitory computer-readable storage medium). In some examples, the processes depicted in sequence diagrams and flowcharts herein can be implemented by any of the systems disclosed herein. The particular series of processing steps in this disclosure are not intended to be limiting. Other sequences of steps may also be performed according to alternative examples. For example, alternative examples of the present disclosure may perform the steps outlined above in a different order. Moreover, the individual steps illustrated in the figures may include multiple sub-steps that may be performed in various sequences as appropriate to the individual step. Furthermore, additional steps may be added or removed depending on the particular applications. One of ordinary skill in the art would recognize many variations, modifications, and alternatives.

In some examples, each process in the figures of this disclosure can be performed by one or more processing units. A processing unit may include one or more processors, including single core or multicore processors, one or more cores of processors, or combinations thereof. In some examples, a processing unit can include one or more special purpose co-processors such as graphics processors, Digital Signal Processors (DSPs), or the like. In some examples, some or all of the processing units can be implemented using customized circuits, such as Application Specific Integrated Circuits (ASICs), or Field programmable gate arrays (FPGAs).

Various techniques (e.g., systems, methods, computer-program products tangibly embodied in a non-transitory computer-readable storage medium, etc.) are described herein for using smell sensor-based Internet-of-Things (IoT) devices to detect and identify individual users based a unique scent or smell print. Interconnected networks of such devices may be used in collaboration, along with other devices (e.g., IoT devices, home monitoring devices, etc.) to track user movements and activities. Further, such smell sensor devices may be used to detect weapons, explosives, narcotics, and other prohibited items that may be concealed and/or not detectable using security cameras. Thus, the data received from the smell sensors and smell-based IoT devices may be used, alone or in combination with other security sensors and systems, to perform safety and security screening within homes, airports or other secure areas, or within any public indoor or outdoor location.

Accordingly, certain aspects described here relate to network devices incorporating smell sensors. Such devices may include specialized hardware and/or software components configured to detect airborne odors and scents, and then analyze the smell data to identify particular individuals, objects, or substances. As noted above, the devices may be smell sensor IoT devices, with wireless network interfaces configured to communicate with other similar IoT devices as well as other network nodes (e.g., television receivers, modems, routers, smartphones, etc.). In some cases, the smell sensor IoT devices may include memory and software-based components capable of storing a catalog of known unique smells, and then comparing current smells or any newly-detected smells to the catalog in order to identify persons and objects. Additionally, in some embodiments, smell sensor IoT devices may include additional sensors including depth sensors (e.g., infrared sensors, ultrasonic sensors, etc.) configured to detect object presence, distance, shape, and movement. The combination of the smell sensors and depth sensors may allow the device to identify individuals and objects with higher confidence, and also to track the movement and activity of multiple distinct individuals or objects. In some embodiments, smell sensor IoT devices also may include a global positioning system (GPS) receiver or other location systems capable of determining the device location, which may be used in collaboration with other device to detect object size and movement, and to "handoff" moving objects to other smell sensor IoT devices within the device network.

Additional aspects described herein relate to coordination and collaboration between multiple smell sensor IoT devices to perform person or object identification, analysis, and tracking. For example, a network of smell sensor IoT devices may communicate location data and data relating to a particular target object (e.g., target location, size, movement, and smell properties). Based on communications between multiple smell sensor IoT devices, a 3D object profile may be generated, and a particular individual or object may be tracked and monitored by a plurality of IoT devices as it moves within an indoor or outdoor location. In such embodiments, smell sensor IoT devices may transmit RF handoff messages to nearby devices, including device identifier data, location data, object identification data and object information, timestamp data, and the like.

Still further aspects described herein relate to using individual smell sensor devices and/or networks of such devices to detect particular objects and substances, such as weapons, explosives, and other dangerous or prohibited materials. Such objects and substances may have unique smell characteristics that may be detected by smell sensor devices. In response to detecting a dangerous or prohibited object or substance, the smell sensor device may take various actions depending on its location, network of nearby devices, nearby users, and the object/substance detected, including broadcasting alerts and performing functions on other connected devices (e.g., activating alarms, locking doors and windows, etc.).

The various embodiments described herein may be implemented on and within one or more different networks and systems, including satellite or terrestrial (e.g. cable) television distribution systems, telecommunications network systems, television distribution computer networks such as the Internet, cellular and other mobile networking systems, and the like. Therefore, although certain examples below are described in terms of specific types of user equipment (e.g., set-top boxes and other television receivers having digital video recorders, etc.) within specific systems (e.g., satellite television distribution systems), it should be understood that similar or identical embodiments may be implemented using other network systems and architectures (e.g., cable television networks, on-demand distribution networks, Internet television computer networks), as well as other user equipment and devices (e.g., personal computers, servers, routers, gaming consoles, smartphones, etc.).

Referring now to FIG. 1, an example home monitoring system 100 including one or more smell sensor devices 180 configured to identify and track individuals and objects at a home or other installation location. Various aspects and embodiments of the present disclosure may be implemented on the home monitoring system 100, which in this example corresponds to a media provider system 100 including a television receiver 140 configured to receive television and/or other video content from television and/or video service providers 110-130 over various different communication networks 115-117. In various embodiments, different television receivers 140 may support various functionality to receive television and/or video content from one or more of the different television providers 110-130 shown in this example, via one or more of the transmission channels 115-117. In some embodiments, the television receiver 140 also may transmit certain data to backend servers 111 and 121 of the television providers 110 and 120, and to computer network-based content providers 130, via the IP network 115, including orders or requests for specific video content resources, status data and statistics relating to video viewing by users, and user and location monitoring data, etc. Additionally, as discussed below, the television receiver 140 may collect data from small sensor devices 180 and/or other home monitoring or IoT devices 190, analyze and transmit the sensor data to back-end service providers 110-130, which may use the data received from the receiver 140 to determine and provide specific and customized video content and/or to communicate to other entities/devices at within the system 100 or elsewhere within an IoT network. In some cases, the data transmitted from the receiver 140 to the one or more content providers 110-130 via the IP network 115 may be secure and/or confidential, and thus may use secure data transmission protocols and/or encryption to protect the user requests, transmissions of user monitoring data, location monitoring data, user tracking data, etc. Additionally, in some embodiments, user and/or location monitoring data may be transmitted via a first network (e.g., IP network 115) while the video content resources themselves may be transmitted via different networks (e.g., television networks 116-117).

In order to perform these features and the additional functionality described below, each of the components and sub-components shown in example system 100, such as television receiver 140, the servers and systems within the satellite, cable, and computer network-based television providers 110-120, presentation device 150, mobile device 160, remote control 170, personal monitoring device 180, and home automation devices/systems 190, etc., may correspond to a single computing device or server, or to a complex computing system including a combination of computing devices, storage devices, network components, etc. Each of these components and their respective subcomponents may be implemented in hardware, software, or a combination thereof. The components shown in system 100 may communicate via communication networks 115-117 (as well as other communication networks not shown in this figure), either directly or indirectly by way of various intermediary network components, such as satellite system components, telecommunication or cable network components, routers, gateways, firewalls, and the like. Although these physical network components have not been shown in this figure so as not to obscure the other elements depicted, it should be understood that any of the network hardware components and network architecture designs may be implemented in various embodiments to support communication between the television receiver 140, television/video service providers 110-130, and other components within system 100.

The television (and/or video) receiver 140 may be implemented using various specialized user equipment devices, such as cable system set-top boxes, satellite system set-top boxes, WiFi or Internet-based set-top boxes, gaming consoles, and the like. In other examples, the receiver 140 may be implemented using (or integrated into) other computing devices such as personal computers, network routers, tablet computers, mobile devices, etc. Thus, the receiver 140 may be implemented as a single computing device or a computing system including a combination of multiple computing devices, storage devices, network components, etc. In some examples, a television receiver 140 may correspond to a primary television receiver (PTR) 240 which may include one or more network interface components (NICs) 141, an electronic programming guide (EPG) user interface component 142, a digital video recorder (DVR) 143, and/or a plurality of tuners 144, and related hardware/software components (e.g., audio/video decoders, descramblers, demultiplexers, etc.) as described below in more detail in FIGS. 2A-2C and 3. In some cases, television receivers 140 may include one or more internal data stores and/or external data stores (e.g., external storage systems, database servers, file-based storage, cloud storage systems, etc.) configured to store television programs (e.g., audio/video files corresponding to television shows or movies, sporting events, live broadcasts, etc.), as well as image data and music/audio content that may be stored on television receivers 140 and output via presentation devices 150 and/or mobile devices 160. In some embodiments, such data stores may reside in a back-end server farm, storage cluster, and/or storage-area network (SAN). As shown in this example, a smell-based monitoring and tracking engine 145 also may be implemented within the television receiver 140 to perform various functionality relating to identifying and monitoring individual users and objects, and transmitting such monitoring data to back-end systems 110-130, and/or performing specific functionality based on certain monitoring data, as described in more detail below.

As shown in this example, television receiver 140 may be configured to communicate with television and/or video service providers 110-130 over multiple communication networks 115-117. As shown in this example, receiver 140 may receive television and/or video content from multiple television providers simultaneously, including a satellite television service provider 110, a cable television service provider 120, and one or more computer-network based television providers. Although three example providers 110-130 are shown in FIG. 1, it should be understood that any number of different television providers may be used in other embodiments, including embodiments in which a receiver 140 is only in communication with one or two of the providers 110-130, and embodiments in which the receiver 140 is in communication with additional satellite and cable television service provider, on-demand television providers, pay-per-view (PPV) television providers, Internet-based television providers, television streaming services, etc. Additionally, although various components within the television receiver 140 and television service providers 110-130 are illustrated as standalone computer systems in this example, any or all of these components may be implemented within and/or integrated into one or more servers or devices of various content distribution systems and other computing architectures. For example, as discussed below in reference to FIGS. 2A-2C and 3, the smell-based monitoring and tracking engine 145 may be implemented solely within a television receiver 140, or may be implemented within a combination of devices within a television/video distribution system, or other location monitoring systems. For example, the smell-based monitoring and tracking engine 145 may be implemented within one or more back-end servers 111, 121, and 130, or as a standalone component and/or in a distributed manner, within other types of content distribution systems, such as terrestrial (e.g., cable) television distribution systems, telecommunications network systems, LAN or WAN computer networks (e.g., the Internet), cellular and other mobile networking systems, and any other computing environment. In any of these examples, the smell-based monitoring and tracking engine 145 may be implemented within (or integrated into) television receivers 140 as shown in FIG. 1, and/or within one or more content servers (e.g., satellite hubs, cable headends, Internet servers, etc.), one or more local computing devices (e.g., televisions, television receivers, set-top boxes, gaming consoles, standalone home monitoring stations, network routers, modems, personal computers, and the etc.), or a combination of server-side devices/services and local devices/services.

Television/video content received and/or decoded by television receiver 140 may be presented via one or more presentation devices 150. Presentation devices 150 may correspond to televisions and other television viewing devices (e.g., home computers, tablet computers, smartphones, etc.). Additionally, various user video output systems 100 may incorporate other user equipment and devices, such as mobile devices 160 and remote control devices 170 configured to communicate with associated television receivers 140 and/or presentation devices 150. User devices 160 may include mobile devices such as smartphones and tablet computers, as well as other various types of user computing devices (e.g., personal computers, laptops, home monitoring/security display devices, weather station displays, digital picture frames, smart watches, wearable computing devices, and/or vehicle-based display devices). In some embodiments, user devices 160 may be associated with specific television receivers 140 and/or specific users/customer accounts associated with the receiver 140 and/or system 100. As shown in FIG. 1, user devices 160 may be configured to receive data from and transmit data to an associated television receiver 140. Additionally or alternatively, user devices 160 may be configured to communicate directly with one or more television service providers 110-130, so that certain transmissions of video content and other functionality (e.g., collecting and transmitting user or location monitoring data, receiving and enforcing user-specific criteria for viewing certain video resources, etc.) may potentially bypass the television receiver 140 in some embodiments.

Different presentation devices 150, user devices 160, and remote control devices 170 may include hardware and software components to support a specific set of output capabilities (e.g., LCD display screen characteristics, screen size, color display, video driver, speakers, audio driver, graphics processor and drivers, etc.), and a specific set of input capabilities (e.g., keyboard, mouse, touchscreen, voice control, cameras, facial recognition, gesture recognition, etc.). Different such devices 150-170 may support different input and output capabilities, and thus different types of user notifications and user inputs in response to notifications (e.g., notifications in response to smell-based detection, identification, and analysis) may be compatible or incompatible with certain devices 150-170. For example, certain notifications generated and output by a television receiver 140, or television/video service providers 110-130, may require specific types of processors, graphics components, and network components in order to be displayed (or displayed optimally) on a user device 160. Additionally, different types of user notifications may include different interactive user response features that require various specific input capabilities for presentation devices 150, user devices 160, and remote control devices 170, such as keyboards, mouses, touchscreens, voice control capabilities, gesture recognition, and the like. In some embodiments, the content of user notifications and/or the user response components may be customized based on the capabilities of the presentation device 150 and/or user device 160 selected to output the notification. Additionally, in some cases, users may establish user-specific preferences, which may be stored in the memory of the television receiver 140, for outputting specific types of user notifications to specific types of presentation devices 150 and/or user devices 160.

System 100 also may include one or more small sensor devices 180, and one or more home monitoring (or personal monitoring) and automation devices or systems 190. Smell sensor devices 180 (discussed below in reference to FIG. 4A), and various other home automation devices 190 (discussed below in reference to FIG. 4B) may include a variety of devices configured to collect and analyze various sensor data proximate to the location of the system 100, including location data (e.g., sights, sounds, smells, etc.), personal user monitoring data and/or device operational status data. As described below in more detail, the smell sensor data received and analyzed by sensors 180 may be used to identify and track particular individuals and objects, as well as initiate communications, alerts, and/or other functionality via output devices and home monitoring devices 190, in response to the data received from smell sensor devices 180.

Smell sensor devices 180, described in more detail below in reference to FIG. 4A, may include, for example, a variety of specialized smell sensing hardware and software components configured to detect airborne odors and scents, and then analyze the smell data to identify particular individuals, objects, or substances. Devices 180 may be home monitoring devices configured for private installation and use and/or IoT devices configured to support public access from other IoT compatible devices. Devices 180 may include one or more network interfaces, as well as memory and software-based components capable of storing a catalog of known smells, and then comparing detected smells to those in the catalog to identify particular individuals and objects. In some embodiments, smell sensor devices 180 also may include additional sensors, including depth sensors (e.g., infrared sensors, ultrasonic sensors, etc.) configured to detect object presence, distance, shape, and movement, and/or location sensors capable of determining the location of device 180 and nearby devices 180-190.

Home monitoring and automation devices and systems 190 may include networks of one or more location-based sensors, device sensors, and/or appliance sensors configured to collect and analyze data relating to a user location, such as user's home, office, etc. An example of a home monitoring and automation system 190, HAS 400, is described below in FIG. 4B. Devices and systems 190 may include personal and/or wearable computing devices configured to detect current health and activity data of a user near the system location 100. As discussed below, in some embodiments, a home monitoring and automation system 190 may be hosted by receiver 140, and may receive data from various sensors configured to monitor the current home environment and the operation of various home devices or appliances. The home monitoring and automation system 190 may collect such user/location data and transmit the data to the receiver 140 and/or other devices within the system 100. Personal and/or wearable computing devices 190 may be configured to detect current health and activity data of a user. Such devices 190 may include various health and activity sensors, heartrate and blood pressure sensors, sleep monitors, temperature monitors, user movement monitors, and personal exercise/fitness sensors that may detect and track the physical state and condition of the user. In some examples, certain personal monitoring devices may be insertable and/or embedded devices with sensors for monitoring various chemicals within the user's bloodstream, such as continuous glucose monitors, alcohol monitoring systems, and other chemical monitoring systems. Personal monitoring devices 190, whether embedded, insertable, wearable, or entirely external to the user (e.g., external monitoring cameras, microphones, and other sensors), may collect personal user biostatistics data and transmit the user data to the receiver 140 and/or other devices within the system 100.

The television receivers 140, television service providers 110-130, presentation devices 150, user devices 160, smell sensor devices 180, and/or home/personal automation and monitoring devices 190, each may include the necessary hardware and software components to establish network interfaces and transmit/receive video signals or data streams, user monitoring data and video output criteria, and/or user interfaces and notifications, etc. Some or all of these devices may include security features and/or specialized hardware (e.g., hardware-accelerated SSL and HTTPS, WS-Security, firewalls, etc.) in order to present the various confidential data transmitted between components (e.g., user and receiver identification data, user monitoring data, user video viewing data, user criteria and access restriction data for certain video resources, etc.), and to prevent hacking and other malicious access attempts within the system 100. In some cases, the television receivers 140 may communicate with television service providers 110-130, user devices 160, and/or monitoring devices 180-190 using secure data transmission protocols and/or encryption for data transfers, for example, File Transfer Protocol (FTP), Secure File Transfer Protocol (SFTP), and/or Pretty Good Privacy (PGP) encryption. Service-based implementations of the system 100 may use, for example, the Secure Sockets Layer (SSL) or Transport Layer Security (TLS) protocol to provide secure connections between the television receivers 140, video content providers 110-130, user devices 160, and/or monitoring devices 180-190. SSL or TLS may use HTTP or HTTPS to provide authentication and confidentiality.

As shown in this example, receiver 140 and providers 110-130, user devices 160, and/or user and location monitoring device/systems 180-190 may communicate over various different types of networks 115-117. For example, network 115 is an Internet Protocol (IP) network, which may use the Internet networking model and/or communication protocols. IP network 115 may include local area networks (LANs), wide area networks (WANs) (e.g., the Internet), and/or various wireless telecommunications networks. For example, when a smell-based monitoring and tracking engine 145 is implemented within a television receiver 140, wireless router, modem, or other local user equipment, then IP network 115 may include wireless local area networks (WLANs) or other short-range wireless technologies such as Bluetooth®, mobile radio-frequency identification (M-RFID), and/or other such communication protocols. In other examples, when at least a portion or component of a user video output engine is implemented remotely as a service in a backend server 111, 121, or 130, or other computer server, satellite hub, cable headend, etc., then IP network 115 may include one or more WANs (e.g., the Internet), various cellular and/or telecommunication networks (e.g., 3G, 4G or EDGE (enhanced data rates for global evolution), WiFi (IEEE 802.11 family standards, or other mobile communication technologies), or any combination thereof. Additionally, system 100 includes satellite networks 116 and cable data networks 117, which may be used in this example for respectively transmitting satellite video data signals and cable video data signals to television receiver 140 and other user equipment. However, it should be understood that IP network 115 also may include various components of satellite communication networks and/or or terrestrial cable networks in some embodiments. For communication between presentation device 150, user devices 160, remote controls 170, and monitoring devices 180-190, and their associated television receivers 140, then communications may include use of a WLAN and/or other short-range wireless technologies. However, for communication between television receivers 140 and remotely located mobile user devices 160 (and/or for user devices 160 that are configured to communicate directly with television service providers 110-130), and remotely-based located monitoring devices/systems 180-190, then communications may include WANs, satellite networks, terrestrial cable networks, and/or cellular or other mobile telecommunication networks, etc.

As discussed above, various components of the system 100 may be implemented as standalone hardware and software systems, and may be implemented within one or more different computer network systems and architectures. For example, in reference to FIGS. 2A-2C and 3, the system 100 may be implemented using one or more user video output services and/or IoT systems executing within back-end server hardware 210 and/or television receiver devices 240 within a satellite television distribution system 200a. However, in other embodiments, the components of a system 100 may be incorporated within various different types of content distribution systems. For example, corresponding embodiments to those described in FIGS. 2A-2C and 3 may be implemented within terrestrial cable television distribution systems 200b, telecommunications network systems, LAN or WAN computer networks (e.g., the Internet), cellular and other mobile networking systems, and the like. In any of these examples, a system 100 may be implemented within (or integrated into) one or more content servers (e.g., satellite hubs, cable head ends, Internet servers, etc.), one or more local computing devices (e.g., televisions, television receivers, set-top boxes, gaming consoles, standalone home monitoring/automation systems, network routers, modems, personal computers, and the etc.), or a combination of server-side devices/services and local devices/services. Thus, although not so limited, an appreciation of various aspects of the present disclosure may be gained from the following discussion in connection with FIGS. 2A-2C and 3.

Figure 2A:
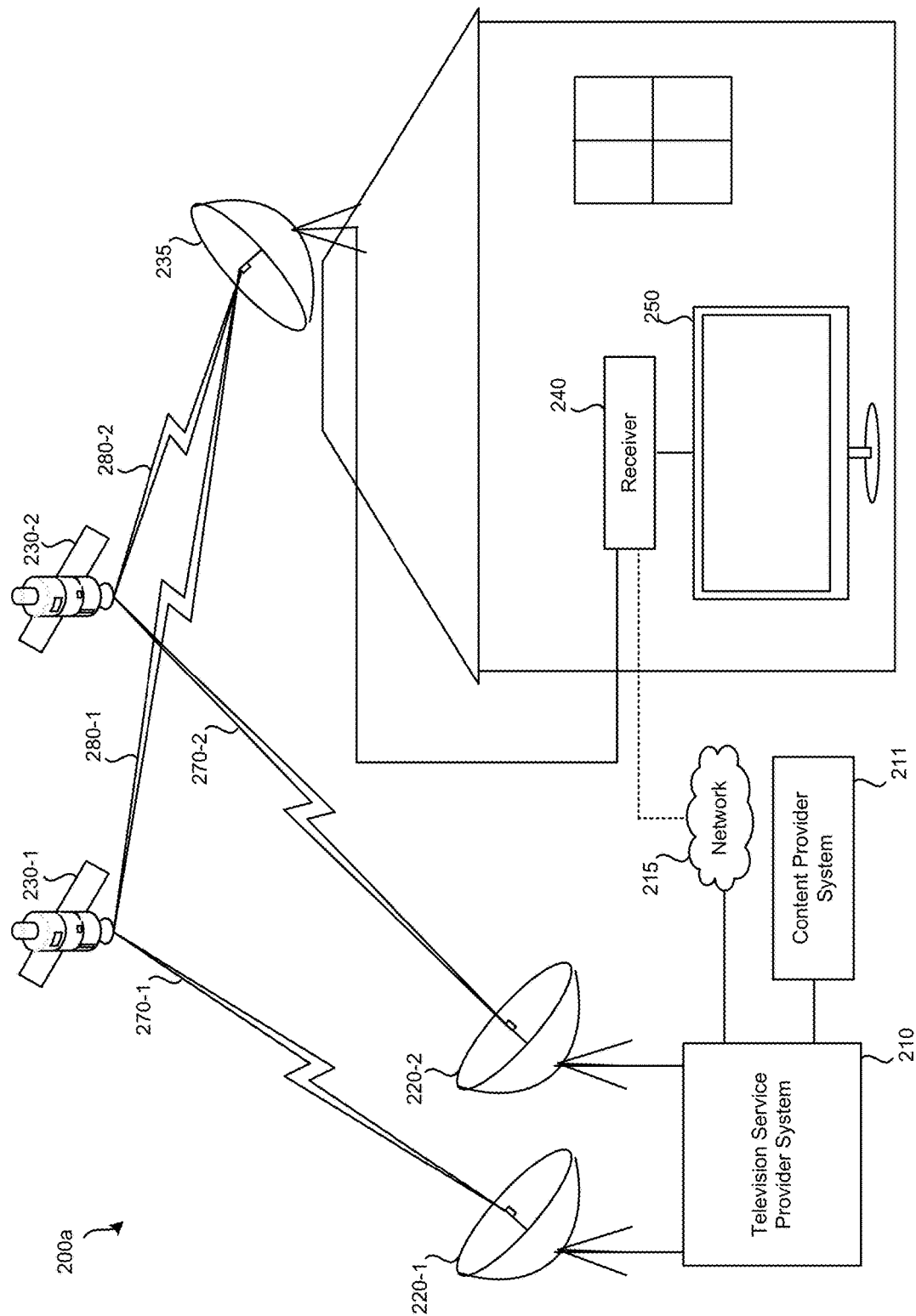
FIG. 2A is a block diagram illustrating an example satellite television distribution system, in accordance with one or more embodiments of the disclosure.

FIG. 2A illustrates an embodiment of a satellite television distribution system 200a. Satellite television distribution system 200a may include: television service provider system 210, satellite transmitter equipment 220-1 and 220-2 (collectively, satellite transmitter equipment 220), satellites 230-1 and 230-2 (collectively, satellites 130), satellite dish 235, receiver 240, and television 250. Alternate embodiments of satellite television distribution system 200a may include fewer or greater numbers of components. While only one satellite dish 235, receiver 240, and television 250 (collectively referred to as "user equipment") are illustrated, it will be appreciated that multiple (e.g., tens, thousands, millions) instances of user equipment may receive television signals from satellites 230. For example, a particular person may have user equipment at multiple homes or other locations.

Television service provider system 210 and satellite transmitter equipment 220 may be operated by a television service provider. A television service provider may distribute television channels, on-demand programming, programming information, and/or other services to viewers. Television service provider system 210 may receive feeds of one or more television channels from various sources, such as content provider system 211. Content provider system 211 may provide television programs, advertisements, and other forms of content. For example, content provider system 211 may be a television network, such as ESPN®. To distribute such television channels to users, feeds of the television channels may be relayed to user equipment via one or more satellites via transponder streams. Satellite transmitter equipment 220 may be used to transmit a feed of one or more television channels from television service provider system 210 to one or more satellites 230. Such satellite feeds may be unidirectional—user equipment may not be able to transmit information back to television service provider system 210 via satellites 230. While a single television service provider system 210 and two satellite transmitter equipment 220 are illustrated as part of satellite television distribution system 200a, it should be understood that multiple instances of transmitter equipment may be used, possibly scattered geographically to communicate with satellites 230. Such multiple instances of satellite transmitting equipment may communicate with the same or with different satellites. Different television channels and content may be transmitted to satellites 230 from different instances of transmitting equipment. For instance, a different satellite dish of transmitting equipment 220 may be used for communication with satellites in different orbital slots.

Satellites 230 may be configured to receive signals, such as streams of television channels, from one or more satellite uplinks, such as from satellite transmitter equipment 220. Satellites 230 may relay received signals from satellite transmitter equipment 220 (and/or other satellite transmitter equipment) to multiple instances of user equipment via transponder streams. Different frequencies may be used for uplink signals 270-1 and 270-2 (collectively, uplink signals 270) from downlink signals 280-1 and 280-2 (collectively, downlink signals 280). Satellites 230 may be in geosynchronous orbit. Each satellite 230 may be in a different orbital slot, such that the signal path between each satellite, uplink stations, and user equipment vary. Multiple satellites 230 may be used to relay television channels from television service provider system 210 to satellite dish 235. Different television channels may be carried using different satellites. Different television channels may also be carried using different transponders of the same satellite; thus, such television channels may be transmitted at different frequencies and/or different frequency ranges. As an example, a first and second television channel may be carried on a first transponder of satellite 230-1. A third, fourth, and fifth television channel may be carried using a different satellite or a different transponder of the same satellite relaying the transponder stream at a different frequency. A transponder stream transmitted by a particular transponder of a particular satellite may include a finite number of television channels, such as seven. Accordingly, if many television channels are to be made available for viewing and recording, multiple transponder streams may be necessary to transmit all of the television channels to the instances of user equipment.

Satellite dish 235 may be a piece of user equipment that is used to receive transponder streams from one or more satellites, such as satellites 230. Satellite dish 235 may be provided to a user for use on a subscription basis to receive television channels provided by the television service provider system 210, satellite uplink 220, and/or satellites 230. Satellite dish 235 may be configured to receive transponder streams from multiple satellites and/or multiple transponders of the same satellite. Satellite dish 235 may be configured to receive television channels via transponder streams on multiple frequencies. Based on the characteristics of receiver 240 and/or satellite dish 235, it may only be possible to capture transponder streams from a limited number of transponders concurrently. For example, a tuner of receiver 240 may only be able to tune to a single transponder stream from a transponder of a single satellite at a time.

Figure 3:
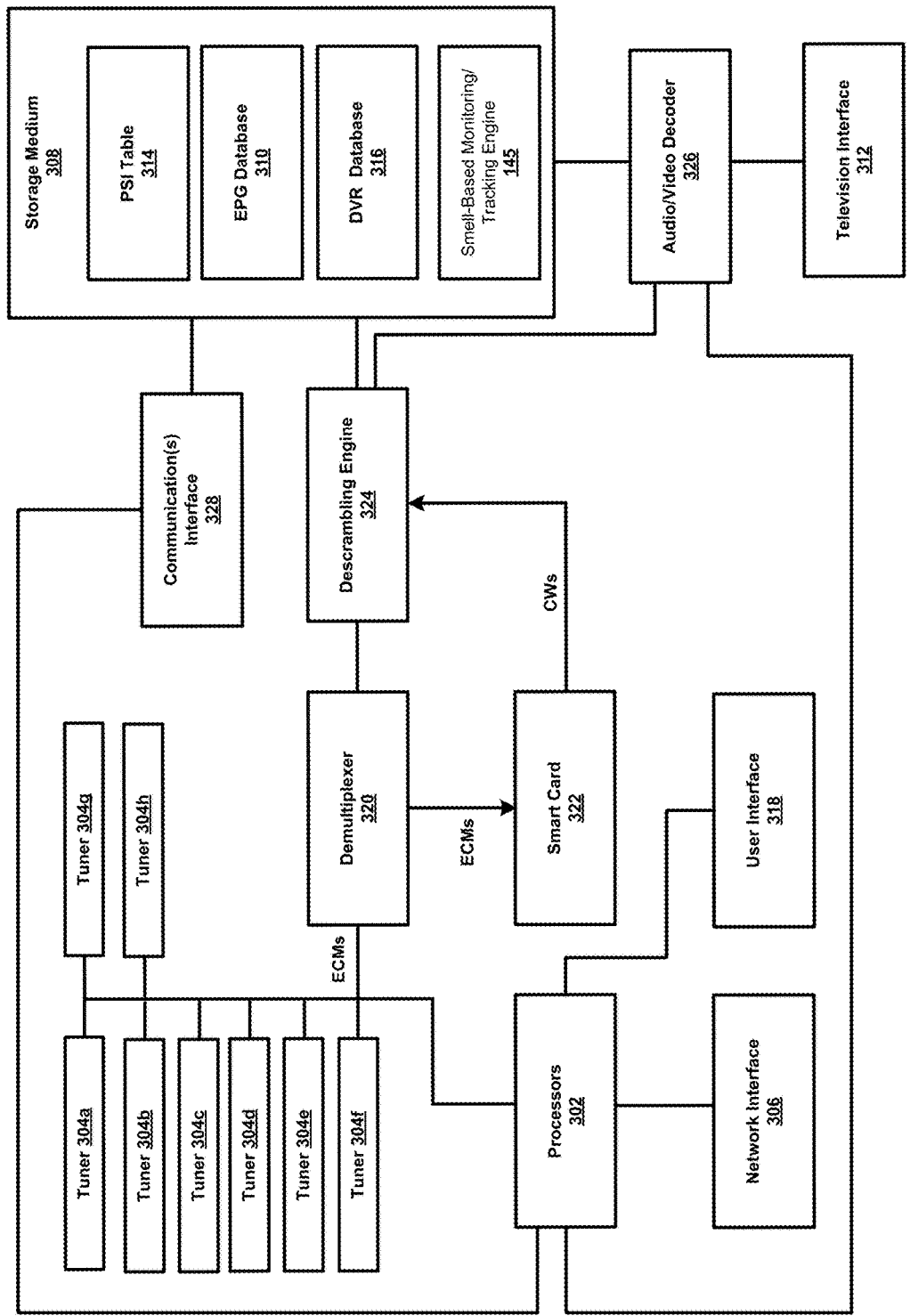
FIG. 3 is a block diagram illustrating an example television receiver device, in accordance with one or more embodiments of the disclosure.

In communication with satellite dish 235, may be one or more sets of receiving equipment. Receiving equipment may be configured to decode signals received from satellites 230 via satellite dish 235 for display on a display or presentation device, such as television 250. Receiving equipment may be incorporated as part of a television or may be part of a separate device, commonly referred to as a set-top box (STB). Receiving equipment may include a satellite tuner configured to receive television channels via a satellite. In FIG. 2A, receiving equipment is present in the form of receiver 240, which may be a STB. Alternatively, receiver 240 may be integrated directly into television 250. Receiver 240 may thus decode signals received via satellite dish 235 and provide an output to television 250. FIG. 3 provides additional detail of receiving equipment.

Television 250 may be used to present video and/or audio decoded by receiver 240. Receiver 240 may also output a display of one or more interfaces to television 250, such as an electronic programming guide (EPG). In some embodiments, a display device other than a television may be used. In some examples, receiver 240 may correspond to receiver 140, television service provider system 210 may correspond to satellite television service provider 110, and network 215 may correspond to IP network 115, described above in FIG. 1. Additionally, various hardware and software components/features of receiver 240 in certain embodiments are described below in FIG. 3.

Uplink signal 270-1 represents a signal between satellite uplink 220-1 and satellite 230-1. Uplink signal 270-2 represents a signal between satellite uplink 220-2 and satellite 230-2. Each of uplink signals 270 may contain streams of one or more different television channels. For example, uplink signal 270-1 may contain a certain group of television channels, while uplink signal 270-2 contains a different grouping of television channels. Each of these television channels may be scrambled such that unauthorized persons are prevented from accessing the television channels.

Transponder stream 280-1 represents a signal between satellite 230-1 and satellite dish 235. Transponder stream 280-2 represents a signal path between satellite 230-2 and satellite dish 235. Each of transponder streams 280 may contain one or more different television channels in the form of transponder streams, which may be at least partially scrambled. For example, transponder stream 280-1 may include a first transponder stream containing a first group of television channels, while transponder stream 280-2 may include a second transponder stream containing a different group of television channels. A satellite may transmit multiple transponder streams to user equipment. For example, a typical satellite may relay 32 transponder streams via corresponding transponders to user equipment. Further, spot beams are possible. For example, a satellite may be able to transmit a transponder stream to a particular geographic region (e.g., to distribute local television channels to the relevant market). Different television channels may be transmitted using the same frequency of the transponder stream to a different geographic region.

FIG. 2A illustrates transponder stream 280-1 and transponder stream 280-2 being received by satellite dish 235. For a first group of television channels, satellite dish 235 may receive a transponder stream of transponder stream 280-1; for a second group of channels, a transponder stream of transponder stream 280-2 may be received. Receiver 240 may decode the received transponder stream. As such, depending on which television channel(s) are desired, a transponder stream from a different satellite (or a different transponder of the same satellite) may be accessed and decoded by receiver 240. Further, while two satellites are present in satellite television distribution system 200a, in other embodiments greater or fewer numbers of satellites may be present for receiving and transmitting transponder streams to user equipment.

Network 215 may serve as a secondary communication channel between television service provider system 210 and receiver 240. Via such a secondary communication channel, bidirectional exchange of data may occur. As such, data may be transmitted to television service provider system 210 via network 215. The connection between network 215 and receiver 240 is illustrated as dotted since this connection allowing communications from receiver 240 to be sent to television service provider system 210 may not be available (e.g., receiver 240 may not have such communication capabilities, receiver 240 may have such capabilities but may not be connected with network 215). For example, even if a receiver is capable of communicating using network 215, communication using network 215 may require that the user has an active account with an internet service provider (ISP). Accordingly, some receivers may only be able to receive data from satellites 230 via receiving equipment, such as satellite dish 235. In other situations, while a user may have an active ISP account, such as via a fiber, cable, or DSL internet connection, equipment failure may occur. For instance, a router through which receiver 240 connects to network 215 may fail or be in need of resetting. Network 215 may be or include the Internet.

FIG. 2A illustrates an example of a satellite-based television channel distribution system. It should be understood that at least some of the aspects of the satellite-based television channel distribution system may be similar to a cable television distribution system. For example, in a cable television system, rather than using satellite transponders, multiple RF channels on a coaxial cable may be used to transmit streams of television channels. Alternatively or additionally, digital data may be transmitted across fiber optic cables. As such, aspects detailed herein may be applicable to cable television distribution systems. Other forms of television distribution networks include broadcast over-the-air systems and IP-based distribution systems.

Figure 2B:
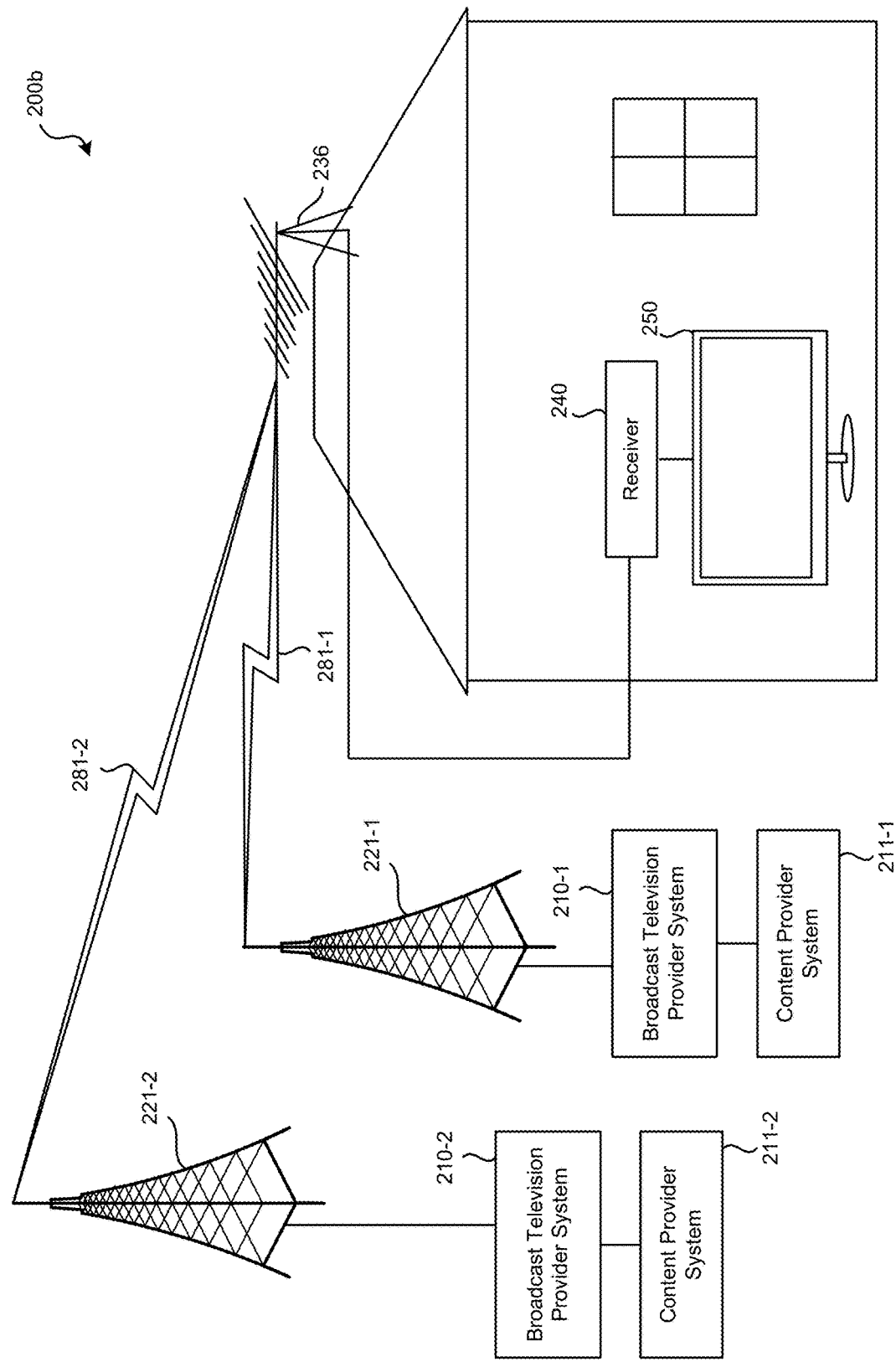
FIG. 2B is a block diagram illustrating an example terrestrial broadcast television system, in accordance with one or more embodiments of the disclosure.

FIG. 2B illustrates an embodiment of a terrestrial broadcast television system 200b. Broadcast television system 200b may include elements similar to satellite television broadcast distribution system 200a, and may include: broadcast television provider system 210-1 and 210-2 (collectively, broadcast television provider system 210), transmitter equipment 221-1 and 221-2 (collectively, transmitter equipment 221), antenna 236, receiver 240, and television 250. Transmitter equipment 221 may include one or more broadcast antennas for transmitting radio frequency broadcasts. For example, receiver 240 may include one or more tuner devices for receiving and decoding broadcast signals received at antenna 236. Alternate embodiments of broadcast television system 200b may include fewer or greater numbers of components. While only one antenna 236, receiver 240, and television 250 (collectively referred to as "user equipment") are illustrated, it will be appreciated that multiple (e.g., tens, thousands, millions) instances of user equipment may receive the broadcasted television signals from transmitter equipment 221.

Broadcast television provider system 210 and transmitter equipment 221 may be operated by a broadcast television service provider. A broadcast television service provider may distribute television channels using radio frequency broadcasts. Broadcast television service provider system 210 may receive feeds of one or more television channels from various sources, such as a content provider system. A content provider system may provide television programs, advertisements, and other forms of content. For example, content provider system may be a television network, such as ABC®. To distribute such television channels to users, feeds of the television channels may be relayed to user equipment via one or more transmitters via broadcast digital transport streams. Transmitter equipment 222 may be used to transmit a feed of one or more television channels from television service provider system 210 for reception by an antenna 236. Such broadcasts are generally unidirectional— user equipment may not be able to transmit information back to television service provider system 210 via antenna 236. Although two broadcast television provider systems 210 and two transmitter equipment 221 are illustrated as part of broadcast television system 200b, it should be understood that one or more instances of transmitter equipment may be used, possibly scattered geographically. In addition, independent broadcast networks may use their own set of one or more transmitter equipment and systems for broadcasting different television channels.

Antenna 236 may be configured to receive signals, such as streams of television channels, from one or more transmitter equipment 221. Broadcast signals 281-1 and 281-2 are depicted as being transmitted from transmitter equipment 221-1 and 221-2, but it will be appreciated that transmitter equipment 221 generally broadcasts streams of television channels over large areas for reception by any appropriate antenna for displaying the broadcast television channel streams without regard to whether any other antennas are receiving the broadcast signals.

In addition, different television channels may be carried on a single broadcast signal 281 using digital subchannels. As an example, a first television channel may be carried on a first digital subchannel of broadcast signal 281 and a second television channel may be carried on a second digital subchannel of broadcast signal 281. In this way, a broadcast television provider may simultaneously broadcast multiple television channel streams using a single transmitter equipment 221 for simultaneous reception by a single antenna 236 and receiver 240.

Antenna 236 may be a piece of user equipment that is used to receive broadcast digital transport streams from one or more transmitters, such as transmitter equipment 221. Antenna 236 may be installed by a user at a suitable point for reception of broadcast signals 281. Antenna 236 may be an omnidirectional antenna, a directional antenna, an amplified antenna, a planar antenna, etc., depending on the configuration. Based on the characteristics of receiver 240 and/or antenna 236, it may only be possible to capture broadcast digital transport streams from a limited number of transmitter equipment concurrently. For example, a tuner of receiver 240 may only be able to tune to a single digital transport stream on a single radio frequency at a time. Receiver 240, however, may include multiple tuners to overcome this limitation.

Receiver 240 may be configured to decode signals received from transmitter equipment 221 via antenna 236 for display on a display or presentation device, such as television 250. Receiver 240 may be incorporated as part of a television or may be part of a separate device, such as a set-top box (STB). Receiver 240 may include tuner configured to receive broadcast television signals. Receiver 240 may thus decode signals received via antenna 236 and provide an output to television 250. Receiver 240 may, in some examples, correspond to receiver 140 described above in FIG. 1. Various hardware and software components/features that may be included in receiver 240 in certain embodiments are described below in FIG. 3.

Television 250 may be used to present video and/or audio decoded by receiver 240. Receiver 240 may also output a display of one or more interfaces to television 250, such as an electronic programming guide (EPG). In some embodiments, a display device other than a television may be used.

Broadcast signal 281-1 represents a signal between transmitter equipment 221-1 and antenna 236. Broadcast signal 281-2 represents a signal path between transmitter equipment 221-2 and antenna 236. Each of broadcast signals 281 may contain one or more different television channels in the form of digital transport streams. For example, broadcast signal 281-1 may include a first digital transport stream containing a first group of television channels, while broadcast signal 281-2 may include a second digital transport stream containing a different group of television channels. Transmitter equipment 221 may transmit multiple digital transport streams to user equipment. For example, a typical transmitter equipment may relay a digital transport stream including one or more television channels in the form of a multiplexed transport stream.

Figure 2C:
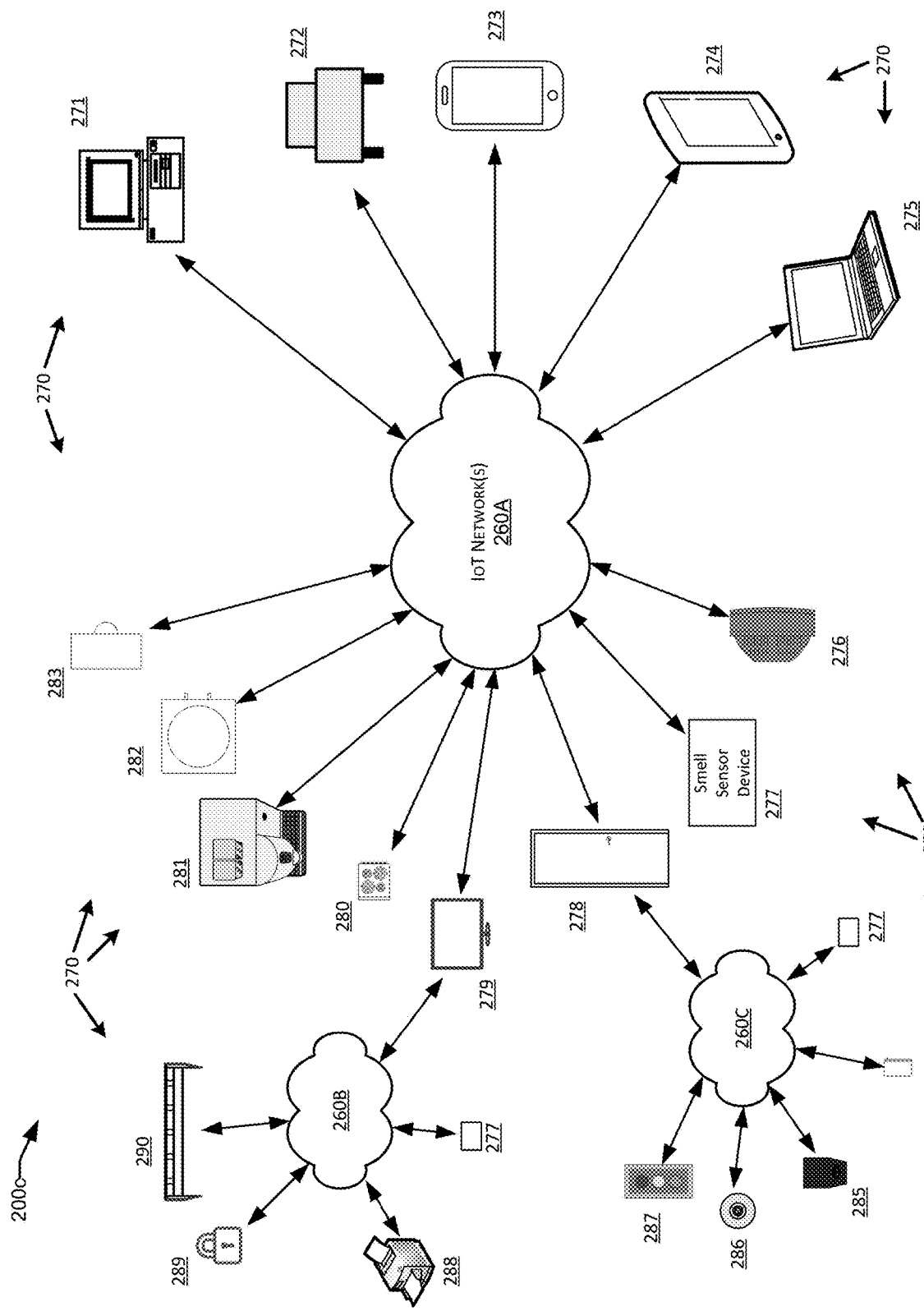
FIG. 2C is a block diagram illustrating an example Internet-of-Things (IoT) system, in which a number of IoT devices are configured to communicate over one or more IoT networks, in accordance with one or more embodiments of the disclosure.

Referring now to FIG. 2C, an example IoT system 200c is shown, in which a number of IoT devices 270 are configured to communicate over one or more IoT networks 260. Although twenty different IoT devices 271-290 (which may be referred to individually or collectively as IoT device(s) 270), and three separate communication networks 260a, 260b, and 260c (which may be referred to individually or collectively as IoT network(s) 260 or IoT interface (s) 260) are shown in this example, it should be understood that this architecture is illustrative only, and any number IoT devices 170 may communicate via any number of different IoT networks 260 in other embodiments.

As noted above, smell sensor devices 180 and/or various home/personal monitoring devices 190 may be IoT devices in some embodiments. Thus, IoT devices 270 may include one or more smell sensor devices 277 and any of the home/location/personal monitoring devices discussed herein. Additionally, IoT network(s) 260 may be built upon IP networks 115 and/or television provider networks 116-117. Similarly, some or all of the IoT device(s) 270 may be electronic devices operating at a home or other installation network and may communicate with the network through television receiver 140 and/or other network devices (e.g., modems, routers, smartphone, etc.) within the system 100. In other examples, certain IoT devices 270 may be installed at separate locations accessible via separate networks or combinations of networks (e.g., including the Internet and one or more cellular/wireless data networks), and thus IoT devices 270 may be widely distributed, both with respect to geography and with respect to the computing environments, networks, and protocols used to access the devices.

In some embodiments, IoT network(s) 260 may correspond to peer-to-peer (P2P) networks formed among the various IoT devices 270. Such networks may be wired or wireless, and may use any combination of known network protocols and technologies, including IP-based networks (e.g., WiFi, IEEE 802.11), RF networks, Bluetooth networks, cellular networks, NFC-based communications, etc. In some examples, IoT network(s) 260 may be based on short-range wireless technologies, and thus IoT devices 270 may discover and communicate with other IoT devices 270 that are within close proximity of each other. Of course, it should be understood that long-range embodiments are also possible, and thus IoT devices 270 in direct or indirect communication might be located in different cities or different countries.

In this example, IoT devices 271-275 may correspond to multi-purpose and/or general purpose computing devices, including personal computer 271, vehicle-based computer system 272, smartphone 273, tablet computer 274, and laptop 275. Such multi-purpose and/or general purpose devices 121-125 may be equipped with user input components (e.g., keyboard, mouse, microphone, touchscreen, etc.) and corresponding software to receive and process a variety of requests from users. Additionally, IoT device 271-275 also may have IP-based network interfaces and the capability to connect to the Internet through one or more wide area network connections (e.g., cellular, WiFi, etc.). Therefore, such multi-purpose and/or general purpose devices 271-275 may correspond to IoT controller devices in many examples discussed herein. In contrast, IoT devices 276-290 in this example may correspond to various appliances, sensors, and/or simpler single-purpose electronic devices. Devices 276-290 also may or may not have Internet connectivity, and also may or may have general user input components. Accordingly, such devices 276-290 may correspond to IoT thing devices in many examples discussed herein. In some cases, IoT thing devices may be passive devices, such as simple electronic devices having RFID tags, NFC tags, simple RF or infrared functionality, etc., which are capable of storing and transmitting device information over short ranges but could not act as IoT controller devices. However, even appliances, sensor devices, and other simple single-purpose devices may act as IoT controller devices in some cases, while general purpose devices such as personal computers 271, vehicle-based systems 272, smartphones 273, tablets 274, etc., may act as IoT thing devices.

Different examples of the interactions between IoT controller devices and IoT thing devices are described in more detail below. In some examples, IoT controller devices may receive and process user requests to perform tasks that will require interactions with one or more different IoT devices (e.g., IoT thing devices), and thus IoT controller devices may perform the processes of discovering accessible IoT thing devices, determining the purpose, status, and functions capable of being performed via the accessible IoT thing devices, and then invoking the appropriate functions on selected IoT thing devices to perform the tasks requested by the user. Thus, IoT controller devices may take the active role in discovering available (e.g., nearby) IoT thing devices, learning their capabilities, and instructing them to perform a desired set of functions, while IoT thing devices may take a more passive role of receiving and responding to requests from IoT controller devices.

However, in some cases, IoT thing devices also may take active roles during IoT device interactions, and perform the functions of IoT controller devices. For example, during a device discovery process, an IoT controller device 273 may broadcast a query to all accessible IoT things devices, seeking an available printer. Although none of the IoT things devices accessible to the IoT controller 273 is a printer, each IoT thing device may be able to connect to a broader network of additional IoT thing devices that are not directly accessible to the IoT controller 273. In this example, a monitor 279 IoT thing device may perform its own device discovery process to locate a printer IoT device 288, and may relay information about the printer device 288 (e.g., a device ID, description, status, location, etc.) to the IoT controller 283.

As another example, an IoT controller device (e.g., vehicle-based system 282) may receive a request from a user to open the front door of the user's house. Through device discovery and inquiry, the IoT controller 272 may identify door 278 as the correct IoT thing device, and may transmit an open request to the door IoT thing device 278. In response, the door IoT device 278 may, based on its own internal programming, decide to turn on one or more lights and/or begin playing music in response to the door being opened. Thus, the door IoT thing device 278 may take the role of an IoT controller by discovering and then instructing one or more light IoT thing devices 286 and/or speaker IoT thing devices 286 to perform the desired functions.

Referring now to FIG. 3, an example block diagram of a primary television receiver (PTR) 240 of FIGS. 2A-2B is shown in accordance with the disclosure. In some examples, one or more secondary television receivers (STRs) at the same location (e.g., home, office, etc.) may be configured in a manner similar to that of the PTR 240. In some examples, the STRs may be configured and arranged to exhibit a reduced functionality as compared to the PTR 240, and may depend at least to a certain degree on the PTR 240 to implement certain features or functionality. The STRs in such examples may be referred to as "thin clients."

In this example, the receiver device 240 may include one or more processors 302, a plurality of tuners 304$a$-$h$, at least one network interface 306, at least one non-transitory computer-readable storage medium 308, at least one EPG database 310, at least one television interface 312, at least one PSI (Program Specific Information) table 314, at least one DVR database 316, at least one user interface 318, at least one demultiplexer 320, at least one smart card 322, at least one descrambling engine 324, at least one decoder 326, and at least one communication interface 328. In other examples, fewer or greater numbers of components may be present. Further, functionality of one or more components may be combined; for example, functions of the descrambling engine 324 may be performed by the processors 302. Still further, functionality of components may be distributed among additional components, and possibly additional systems such as, for example, in a cloud-computing implementation.

The processors 302 may include one or more specialized and/or general-purpose processors configured to perform processes such as tuning to a particular channel, accessing and displaying EPG information, and/or receiving and processing input from a user. For example, the processors 302 may include one or more processors dedicated to decoding video signals from a particular format, such as according to a particular MPEG (Motion Picture Experts Group) standard, for output and display on a television, and for performing or at least facilitating decryption or descrambling.

The tuners 304a-h may be used to tune to television channels, such as television channels transmitted via satellites 220 and/or transmitter equipment 22. Each one of the tuners 304a-h may be capable of receiving and processing a single stream of data from a satellite transponder, or a cable RF channel, at a given time. As such, a single tuner may tune to a single transponder or, for a cable network, a single cable channel. Additionally, one tuner (e.g., tuner 304a) may be used to tune to a television channel on a first transponder stream for display using a television, while another tuner (e.g., tuner 304b) may be used to tune to a television channel on a second transponder for recording and viewing at some other time. If multiple television channels transmitted on the same transponder stream are desired, a particular tuner (e.g., tuner 304c) may be used to receive the signal containing the multiple television channels for presentation and/or recording of each of the respective multiple television channels, such as in a PTAT (Primetime Anytime) implementation for example. Although eight tuners 304a-h are shown in this example, the receiver device 240 may include more or fewer tuners (e.g., three tuners, sixteen tuners, etc.), and the features of the disclosure may be implemented similarly and scale according to the number of tuners of the receiver 240.

The network interface 306 may be used to communicate via alternate communication channel(s) with a service provider. For example, the primary communication channel between television service providers 110-120 and the receiver device 240 may be via satellite or cable networks 116 and 117, which may be unidirectional to the receiver 240, and another communication channel between the television service providers 110-120 and the receiver 240, which may be bidirectional, may be via the network 115. In general, various types of information may be transmitted and/or received via the network interface 306.

The storage medium 308 may represent a non-transitory computer-readable storage medium. The storage medium 308 may include memory and/or a hard drive. The storage medium 308 may be used to store information received from one or more satellites and/or information received via the network interface 306. For example, the storage medium 308 may store information related to the EPG database 310, the PSI table 314, and/or the DVR database 316, among other elements or features, such as the smell-based monitoring and tracking engine 145 discussed above. Recorded television programs may be stored using the storage medium 308 and ultimately accessed therefrom.

The EPG database 310 may store information related to television channels and the timing of programs appearing on such television channels. Information from the EPG database 310 may be used to inform users of what television channels or programs are available, popular and/or provide recommendations. Information from the EPG database 310 may be used to generate a visual interface displayed by a television that allows a user to browse and select television channels and/or television programs for viewing and/or recording. Information used to populate the EPG database 310 may be received via the network interface 306 and/or via satellite, cable, or computer networks 115-117. For example, updates to the EPG database 310 may be received periodically or at least intermittently via satellite or cable television provider. The EPG database 310 may serve as an interface for a user to control DVR functions of the receiver 240, and/or to enable viewing and/or recording of multiple television channels simultaneously.

The decoder 326 may convert encoded video and audio into a format suitable for output to a display device. For instance, the decoder 326 may receive MPEG video and audio from the storage medium 308 or the descrambling engine 324, to be output to a television. MPEG video and audio from the storage medium 308 may have been recorded to the DVR database 316 as part of a previously-recorded television program. The decoder 326 may convert the MPEG video and audio into a format appropriate to be displayed by a television or other form of display device and audio into a format appropriate to be output from speakers, respectively. The decoder 326 may be a single hardware element capable of decoding a finite number of television channels at a given time, such as in a time-division arrangement. In the example embodiment, eight television channels may be decoded concurrently or simultaneously.

The television interface 312 output a signal to a television, or another form of display device, in a proper format for display of video and play back of audio. As such, the television interface 312 may output one or more television channels, stored television programming from the storage medium 308, such as television programs from the DVR database 316 and/or information from the EPG database 310 for example, to a television for presentation.

The PSI table 314 may store information used by the receiver 240 to access various television channels. Information used to populate the PSI table 314 may be received via satellite, or cable, through the tuners 304a-h and/or may be received via the network interface 306 over the computer network 115 from one or more of the providers 110-130. Information present in the PSI table 314 may be periodically or at least intermittently updated. Information that may be present in the PSI table 314 may include: television channel numbers, satellite identifiers, frequency identifiers, transponder identifiers, ECM PIDs (Entitlement Control Message, Packet Identifier), one or more audio PIDs, and video PIDs. A second audio PID of a channel may correspond to a second audio program, such as in another language. In some examples, the PSI table 314 may be divided into a number of tables, such as a NIT (Network Information Table), a PAT (Program Association Table), and a PMT (Program Management Table).

Table 1 below provides a simplified example of the PSI table 314 for several television channels. It should be understood that in other examples, many more television channels may be represented in the PSI table 314. The PSI table 314 may be periodically or at least intermittently. As such, television channels may be reassigned to different satellites and/or transponders, and the PTR 210 may be able to handle this reassignment as long as the PSI table 314 is updated.

TABLE 1

| Channel | Satellite | Transponder | ECM PID | Audio PIDs | Video PID |
|---------|-----------|-------------|---------|------------|-----------|
| 4 | 1 | 2 | 27 | 2001 | 1011 |
| 5 | 2 | 11 | 29 | 2002 | 1012 |
| 7 | 2 | 3 | 31 | 2003 | 1013 |
| 13 | 2 | 4 | 33 | 2003, 2004 | 1013 |

It should be understood that the values provided in Table 1 are for example purposes only. Actual values, including how satellites and transponders are identified, may vary. Additional information may also be stored in the PSI table 314. Video and/or audio for different television channels on different transponders may have the same PIDs. Such television channels may be differentiated based on which satellite and/or transponder to which a tuner is tuned.

DVR functionality of the receiver device 240 may permit a television channel to be recorded for a period of time. The DVR database 316 may store timers that are used by the processors 302 to determine when a television channel should be tuned to and recorded to the DVR database 316 of storage medium 308. In some examples, a limited amount of space of the storage medium 308 may be devoted to the DVR database 316. Timers may be set by the television/video service providers 110=130 and/or one or more users of the receiver 240. DVR functionality of the receiver device 240 may be configured by a user to record particular television programs. The PSI table 314 may be used by the receiver device 240 to determine the satellite, transponder, ECM PID, audio PID, and video PID.

The user interface 318 may include a remote control, physically separate from receiver device 240, and/or one or more buttons on the receiver device 240 that allows a user to interact with the receiver device 240. The user interface 318 may be used to select a television channel for viewing, view information from the EPG database 310, and/or program a timer stored to the DVR database 316 wherein the timer may be used to control the DVR functionality of the receiver device 240.

Referring back to the tuners 304*a*-*h*, television channels received via satellite may contain at least some encrypted or scrambled data. Packets of audio and video may be scrambled to prevent unauthorized users, such as nonsubscribers, from receiving television programming without paying the television service providers 110-130. When one of the tuners 304*a*-*h* is receiving data from a particular transponder of a satellite, the transponder stream may be a series of data packets corresponding to multiple television channels. Each data packet may contain a PID, which in combination with the PSI table 314, can be determined to be associated with a particular television channel. Particular data packets, referred to as ECMs may be periodically transmitted. ECMs may be encrypted; the receiver device 240 may use the smart card 322 to decrypt ECMs.

The smart card 322 may function as the CA (Controlled Access) which performs decryption of encryption data to obtain control words that are used to descramble video and/or audio of television channels. Decryption of an ECM may only be possible when the user (e.g., an individual who is associated with the receiver device 240) has authorization to access the particular television channel associated with the ECM. When an ECM is received by the demultiplexer 320 and the ECM is determined to correspond to a television channel being stored and/or displayed, the ECM may be provided to the smart card 322 for decryption.

When the smart card 322 receives an encrypted ECM from the demultiplexer 320, the smart card 322 may decrypt the ECM to obtain some number of control words. In some examples, from each ECM received by the smart card 322, two control words are obtained. In some examples, when the smart card 322 receives an ECM, it compares the ECM to the previously received ECM. If the two ECMs match, the second ECM is not decrypted because the same control words would be obtained. In other examples, each ECM received by the smart card 322 is decrypted; however, if a second ECM matches a first ECM, the outputted control words will match; thus, effectively, the second ECM does not affect the control words output by the smart card 322. When an ECM is received by the smart card 322, it may take a period of time for the ECM to be decrypted to obtain the control words. As such, a period of time, such as about 0.2-0.5 seconds, may elapse before the control words indicated by the ECM can be obtained. The smart card 322 may be permanently part of the receiver device 240 or may be configured to be inserted and removed from the receiver device 240.

The demultiplexer 320 may be configured to filter data packets based on PIDs. For example, if a transponder data stream includes multiple television channels, data packets corresponding to a television channel that are not desired to be stored or displayed by the user may be ignored by the demultiplexer 320. As such, only data packets corresponding to the one or more television channels desired to be stored and/or displayed may be passed to either the descrambling engine 324 or the smart card 322; other data packets may be ignored. For each channel, a stream of video packets, a stream of audio packets and/or a stream of ECM packets may be present, each stream identified by a PID. In some examples, a common ECM stream may be used for multiple television channels. Additional data packets corresponding to other information, such as updates to the PSI table 314, may be appropriately routed by the demultiplexer 320.

The descrambling engine 324 may use the control words output by the smart card 322 in order to descramble video and/or audio corresponding to television channels for storage and/or presentation. Video and/or audio data contained in the transponder data stream received by the tuners 304*a*-*h* may be scrambled. The video and/or audio may be descrambled by the descrambling engine 324 using a particular control word. The control word output by the smart card 322 to be used for successful descrambling may be indicated by a scramble control identifier present within the data packet containing the scrambled video or audio. Descrambled video and/or audio may be output by the descrambling engine 324 to the storage medium 308 for storage, such as part of the DVR database 316 for example, and/or to the decoder 326 for output to a television or other presentation equipment via the television interface 312.

The communication interface 328 may be used by the receiver device 240 to establish a communication link or connection between the receiver device 240 and one or more of the computing systems and devices as shown in FIGS. 1 and 2A-2C, discussed further below. It is contemplated that the communication interface 328 may take or exhibit any form as desired, and may be configured in a manner so as to be compatible with a like component or element incorporated within or to a particular one of the computing systems and devices as shown in FIGS. 1 and 2A-2C, and further may be defined such that the communication link may be wired and/or or wireless. Example technologies consistent with the principles or aspects of the present disclosure may include, but are not limited to, Bluetooth®, WiFi, NFC (Near Field Communication), HomePlug®, and/or any other communication device or subsystem similar to that discussed below.

For brevity, the receiver device 240 is depicted in a simplified form, and may generally include more or fewer elements or components as desired, including those configured and/or arranged for transmitting receiver identification data, subscription packages selections, television viewing data, and the like, to television provider servers, receiving authorization codes, and using the authorization codes to program/configure the components of the receiver device 240 to decode and output authorized television content, in accordance with the principles of the present disclosure. For example, the receiver 240 is shown in FIG. 3 to include an instance of the smell-based monitoring and tracking engine 145 as mentioned above in connection with FIG. 1. In other examples, the receiver device 240 may include a user video output 245, that is configured to communicate with a corresponding service 240 in a back-end server of a content provider (e.g., 111, 121, or 130). While shown stored to the storage medium 308 as executable instructions, a smell-based monitoring and tracking engine 145 (and/or service) could, wholly or at least partially, be stored to the processor(s) 302 of the receiver 240. Further, some routing between the various modules of receiver 240 has been illustrated. Such illustrations are for exemplary purposes only. The state of two modules not being directly or indirectly connected does not indicate the modules cannot communicate. Rather, connections between modules of the receiver 240 are intended only to indicate possible common data routing. It should be understood that the modules of the receiver 240 may be combined into a fewer number of modules or divided into a greater number of modules.

Additionally, although not explicitly shown in FIG. 3, the receiver device 240 may include one or more logical modules configured to implement a television steaming media functionality that encodes video into a particular format for transmission over the Internet such as to allow users to remotely view and control a home cable, satellite, or personal video recorder system from an Internet-enabled computer with a broadband Internet connection. The Slingbox® by Sling Media, Inc. of Foster City, Calif., is one example of a product that implements such functionality. Further, the receiver 240 may be configured to include any number of other various components or logical modules that are implemented in hardware, software, firmware, or any combination thereof, and such components or logical modules may or may not be implementation-specific.

Figure 4A:
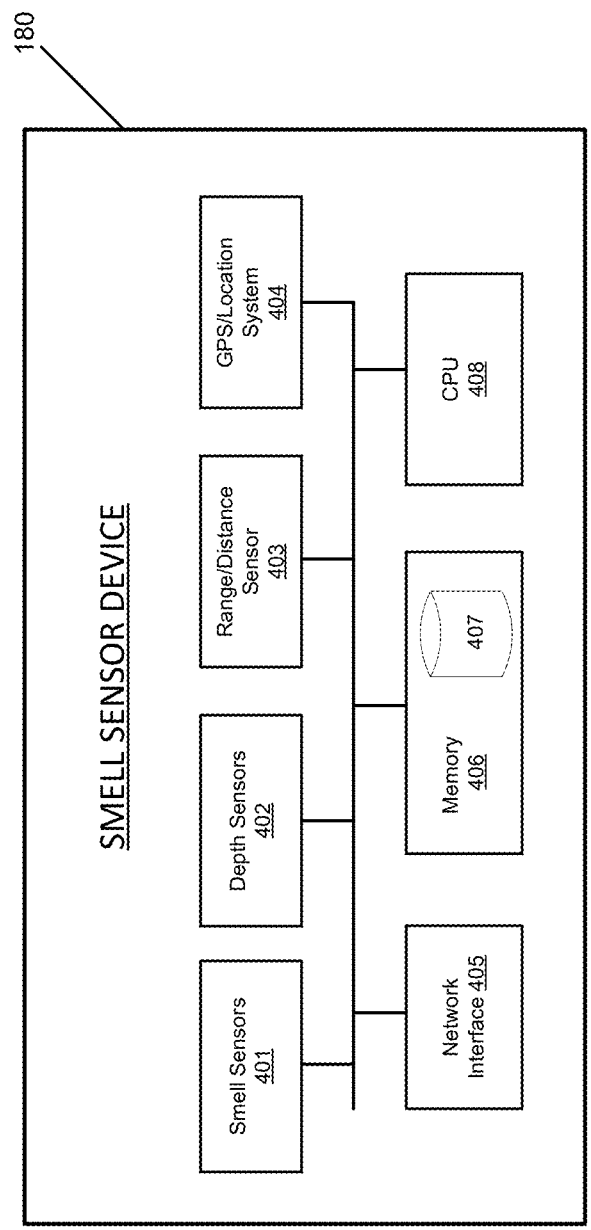
FIG. 4A is a block diagram illustrating the components of a smell sensor device, in accordance with one or more embodiments of the disclosure.

Referring now to FIG. 4A, a block diagram is shown illustrating the components of an example smell sensor device 180. As shown in this example, smell sensor device 180 may include one or more aroma sensing detector 401 configured to capture, detect, and analyze detect airborne odors and scents in the proximity of the sensor device 180. Smell sensors 401 may include any type of odor sensing technology, such as chemical-based receptor sensors that react when coming into contact with particular compounds that correspond to specific odors. In various embodiments, sensors 401 may include one or more metal-oxide semiconductor (MOSFET) devices in which the charge of molecules entering the sensor may affect the electric field within the sensor in a unique and detectable way. Smell sensors 401 also may include conducting organic polymers that conduct electricity and/or polymer composites that consist of nonconducting polymers to which conducting material may be added. Additionally, sensors 401 may include mass per unit area measuring devices, such as quartz crystal microbalance, that detects changes in mass per unit area by measuring a change in frequency of the quartz crystal resonator. Further, sensors 401 may include one or more microelectromechanical systems (MEMS), such as surface acoustic waves (SAWs), that detect the modulation of surface acoustic waves. In a specific example of a smell sensor 401, a sensor chip may include nanowires made of tin dioxide on many individual sensors. In this example, the sensor chip may calculate specific signal patterns based on the resistance changes of the individual sensors. The resistance changes may depend on the molecules in ambient air, and thus may differ for the different aromas. This technique may use a light-emitting diode integrated into the housing of sensor 401 that irradiates the nanowires with UV light. Therefore, an initially very high electrical resistance of tin dioxide may decrease as floating molecules within the air (which contain the aroma) attach to the tin dioxide surface and are detected by the resistance change.

In some embodiments, smell sensor device 180 also may include one or more depth sensors 402. Depth sensors 402 may include a combination of cameras, passive or active infrared sensors, ultrasonic sensors, etc., which may work individually or combination to identify objects, determine physical size, shape, and distance, as well as detecting motion of the object. For instance, in some embodiments, depth sensors 402 may include an infrared projector (to transmit invisible near-infrared light) and a monochrome CMOS sensor (or other similar sensor), which may be used together to measure the precise distance (e.g., by measuring round-trip travel time for the infrared light) between the smell sensor device 180 and each point on the individuals and objects near the sensor device 180. Additionally, depth sensors 402 may include one or more cameras (e.g., RGB color VGA video cameras) which may detect color components and may assist in facial and body recognition.

In addition to smell sensors 401 and depth sensors 402, in various embodiments the smell sensor device 180 may include various other sensors and specialized hardware to provide additional features and/or improved functionality for the smell-based detection and monitoring/tracking of individuals and objects. For example, smell sensor devices 180 also may include ultrasonic or optical range/distance measuring devices 403 and/or GPS receivers or other location systems 404 to determine the precise location of the smell sensor device 180. Different types of location systems 404 may either determine an absolute location (e.g., GPS coordinates) of the sensor device 180, or relative location with respect to one or more other devices at the same location/computing environment. In some cases, differential GPS and other highly accurate GPS-based systems may allow the position of the smell sensor device 180, which may generally (though not necessarily) be stationary at a fixed location, to be determined to within a very small distance range (e.g., within an inch). Although not shown in this example, additional types of sensors may be included within various embodiments of smell sensor devices 180. Such additional types of sensors may include motion and gyroscopic sensors to detect movement of the sensor device 180, compasses to detect orientation, passive IR motion sensors, microphones, ultrasonic sensors, etc.

In this example, smell sensor device 180 also includes one or more network interfaces 405 (e.g., IP computer network interface, cellular and/or WiFi interface, short-range wireless interface, etc.), which may be used to transmit sensor data (e.g., scent data, individual/object identification data, individual/object location data, individual/object size, shape, and movement data, etc.). As noted above, the various sensor data collected by smell sensor devices 180 may be transmitted via network interfaces 405 to a television receiver 140 (or modem, router wireless device 420, etc.) or to a controller device within an HAS 400 or IoT network. Network interfaces 404 also may be used to transmit configuration instructions and other data (e.g., odor print/smell print characteristics for different individuals or objects) to the smell sensor device 180.

Finally, smell sensor device 180 may include one or more memory devices/systems 406 and one or more processing units 408 to store and execute the computer instructions that support the various functionality described herein. As shown in this example, the memory 406 of the smell sensor device 180 may include one or more data stores 407 that include the unique smell data/odor data characteristics associated with a plurality of different objects, substances, and individuals. For example, humans continuously shed large numbers of tiny skin flakes, called rafts, that include unique combinations of skin cells, hormones, enzymes, fungus, bacteria, parasites, and/or hygiene products. A person's skin rafts are unique to that individual, and the skin rafts of different individuals are not identical, even for closely related individuals or identical twins. The lighter skin rafts shed from a perform may be carried by air currents into the sensor device 180 where it is received and analyzed. Inanimate objects and substances may similarly have unique odor/scent profiles or characteristics (which may be referred to as a smell print). Thus, in this example, database 407 may include one or more skin raft profiles for multiple individuals associated with the location of the sensor device 180, as well as a catalog of object/substance scents that may be detected and identified by the sensor device 180. In some cases, a sensor device 180 may store the "smell print" profile data for a set of individuals associated with the installation location (e.g., family members for smell sensor devices of a home monitoring system, coworkers for smell sensor devices of a workplace security system, etc.). Additionally or alternatively, an operational smell sensor device 180 may detect and store smell print profile data for each new person it detects in the proximity of the sensor device 180. In still other embodiments, a database of smell print profile data for a number of persons and/or specific objects or substances to be detected, may be transmitted from a central server (e.g., backend servers 110, 120, or 130) to each of a plurality of television receivers 140 or other client devices. Additionally, individual smell sensor devices 180 may collect and store aroma/odor data for any newly detected persons, objects, or substances, and the transmit the corresponding smell print profile data to other smell sensor devices 180 in the network, and/or to one or more central server systems.

Figure 4B:
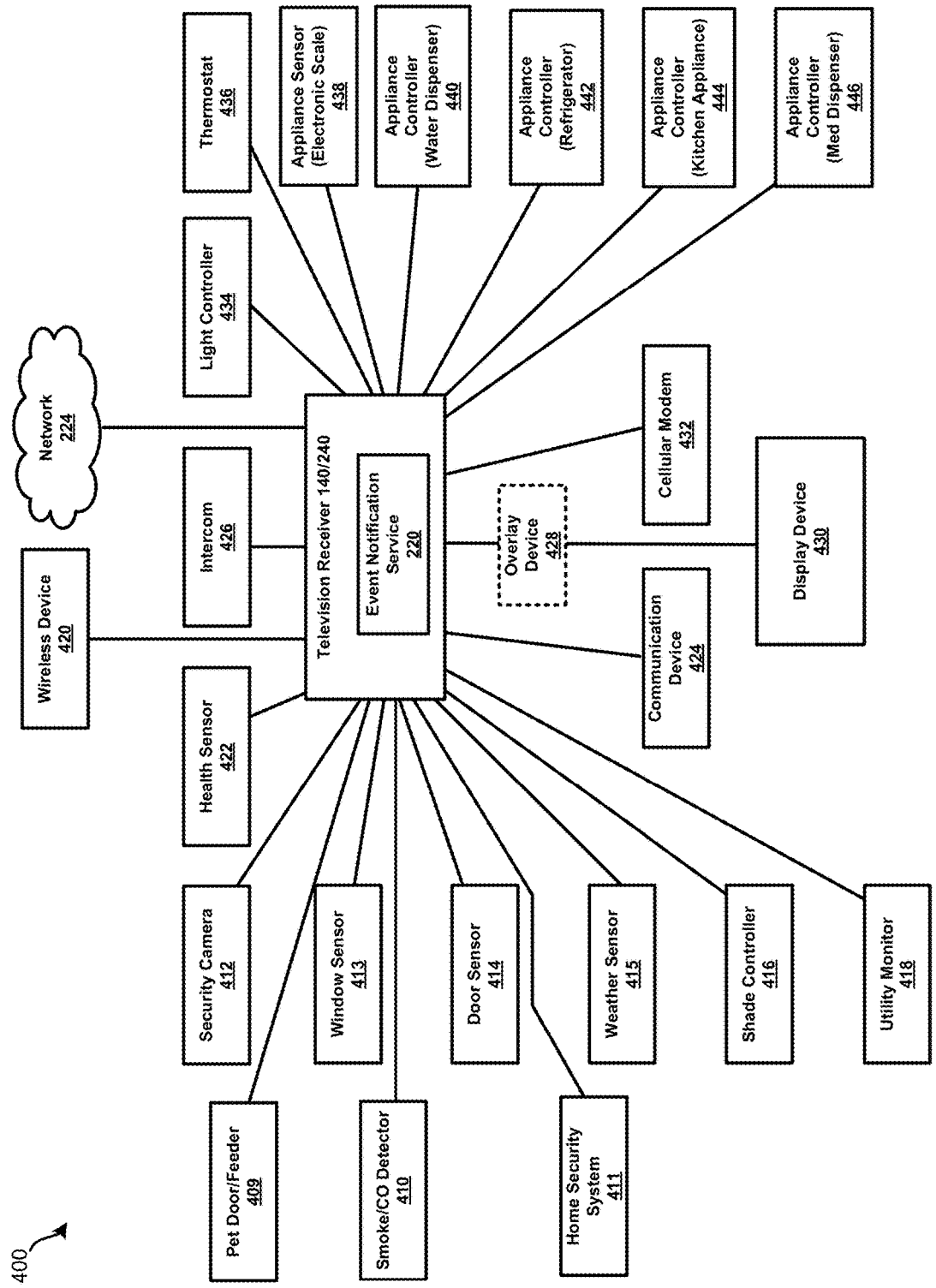
FIG. 4B is a block diagram illustrating a home automation system, in accordance with one or more embodiments of the disclosure.

Referring now to FIG. 4B, an example home automation system (HAS) 400 is shown in accordance with certain embodiments. As discussed above, home monitoring and automation devices and systems 400 may be used separately from or in conjunction with one or more smell sensor devices 180. For example, home monitoring and automation devices and systems 400 may be used to monitor the same or related users and locations, and the sensor data may be combined with data from one or more smell sensor devices 180, in order to more accurately and efficiently identify particular users, objects, or substances. Additionally, as discussed below, smell data analyses and resulting determinations of particular users, objects, or substances may cause a smell-based monitoring and tracking engine 145 to initiate communications and/or actions which may invoke one or more electronic devices within the home automation system (HAS) 400. Thus, although the smell sensor device 180 was described in detail in FIG. 4A, one or more such devices can be included and incorporated into the HAS 400 in FIG. 4B.

In this example, the home automation system 400 may be hosted by a receiver device 240 as shown in FIGS. 2A-2B and 3 (which also may correspond to receiver 140 of FIG. 1), and thus the receiver 240 may be considered a home automation gateway device or system. An overlay device 428 is also shown in FIG. 4B. In another example, the HAS 400 may be hosted by the overlay device 428 of FIG. 4B, and thus the overlay device 428 may be considered a home automation gateway device or system. Still other examples are possible. For instance, in some example, features or functionality of the overlay device 428 may be wholly or at least partially incorporated into the receiver device 240 (and vice versa), so that the HAS 400 may be considered to be hosted or managed or controlled by both receiver 240 and the overlay device 428. In this manner, the receiver 240, the overlay device 428, or any combination of functionality thereof, may be considered the central feature or aspect of the example HAS 400. Additionally, in still other examples, the HAS 400 might not be hosted by a receiver 240 or an overlay device, but may be operated by a standalone device 190 that may communicate with one or more receivers via an IP network 115 or other local communication protocols.

In this example, the receiver device 240 and/or the overlay device 428 may be configured and/or arranged to communicate with multiple sensor devices, including at least the various in-home, personal/wearable, or on-residence home automation related systems and/or devices shown in FIG. 4B. Some examples of sensor devices may include, but are not limited to: at least one pet door/feeder 409, at least one smoke/$CO_2$ detector 410, a home security system 411, at least one security camera 412, at least one window sensor 413, at least one door sensor 414, at least one weather sensor 415, at least one shade controller 416, at least one utility monitor 418, at least one third party device 420, at least one health sensor 422, at least one communication device 424, at least one intercom 426, at least one overlay device 428, at least one display device 430, at least one cellular modem 432, at least one light controller 434, at least one thermostat 436, and one or more appliance sensors/controllers (e.g., scale sensor 438, water dispenser controller 440, refrigerator controller 442, a kitchen appliance controller 444, and an electronic medication dispenser 446). It should be understood that the HAS 400 depicted in FIG. 4B is just one example, and that other examples are possible as discussed further below.

In various embodiments, each of the elements of FIG. 4B, with which the receiver device 240 communicates, may use different communication standards. For example, one or more elements may use or otherwise leverage a ZigBee® communication protocol, while one or more other devices may communicate with the receiver 240 using a Z-Wave® communication protocol. As another example, one or more elements may use or otherwise leverage a WiFi communication protocol, while one or more other devices may communicate with the receiver 240 using a Bluetooth communication protocol. Any combination thereof is further contemplated, and other forms of wireless communication may be used by particular elements of FIG. 4B to enable communications to and from the receiver 240, such as any particular IEEE (Institute of Electrical and Electronics Engineers) standard or specification or protocol, such as the IEEE 802.11 technology for example.

In some examples, a separate device may be connected with the receiver 240 to enable communication with the smart home automation systems or devices of FIG. 4B. For instance, the communication device 424 as shown coupled with the receiver device 240 may take the form of a dongle. In some examples, the communication device 424 may be configured to allow for Zigbee®, Z-Wave®, and/or other forms of wireless communication. In some example, the communication device 424 may connect with the receiver 240 via a USB (Universal Serial Bus) port or via some other type of (e.g., wired) communication port. Accordingly, the communication device 424 may be powered by the receiver 240 or may be separately coupled with another different particular power source. In some examples, the receiver 240 may be enabled to communicate with a local wireless network and may use communication device in order to communicate with devices that use a ZigBee® communication protocol, Z-Wave® communication protocol, and/or some other wireless communication protocols.

In some examples, the communication device 424 may also serve to allow or enable additional components to be connected with the receiver device 240. For instance, the communication device 424 may include additional audio/video inputs (e.g., HDMI), component, and/or composite inputs to allow for additional devices (e.g., Blu-Ray players) to be connected with the receiver 240. Such a connection may allow video comprising home automation information to be "overlaid" with television programming, both being output for display by a particular presentation device. Whether home automation information is overlaid onto video on display may be triggered based on a press of a remote control button by an end-user.

Regardless of whether the receiver 240 uses the communication device 242 to communicate with any particular home automation device shown in FIG. 4B or other particular home automation device not explicitly shown in receiver 240, the receiver 240 may be configured to output home automation information for presentation via the display device 430. It is contemplated that the display device 430 could correspond to any particular one of the televisions and/or user devices describes above in FIGS. 1-3. Still other examples are possible. Such information may be presented simultaneously, concurrently, in tandem, etc., with any particular television programming received by the receiver 240 via any particular communication channel as discussed above. It is further contemplated that the receiver 240 may also, at any particular instant or given time, output only television programming or only home automation information based on preferences or commands or selections of particular controls within an interface of or by any particular end-user. Furthermore, an end-user may be able to provide input to the receiver 240 to control the HAS 400, in its entirety as hosted by the receiver 240 or by the overlay device 428, as discussed further below.

In some examples (indicated by intermittent line in FIG. 4B), the overlay device 428 may be coupled with the receiver 240 to allow or enable home automation information to be presented via the display device 430. It is contemplated that the overlay device 428 may be configured and/or arranged to overlay information, such as home automation information, onto a signal that will ultimately enable the home automation information to be visually presented via the display device 430. In this example, the receiver 240 may receive, decode, descramble, decrypt, store, and/or output television programming. The receiver 240 may output a signal, such as in the form of an HDMI signal. Rather than being directly input to the display device 430, however, the output of the receiver 240 may be input to the overlay device 428. Here, the overlay device 428 may receive video and/or audio output from the receiver 240.

The overlay device 428 may add additional information to the video and/or audio signal received from the receiver 240 so as to modify or augment or even "piggyback" on the same. That video and/or audio signal may then be output by the overlay device 428 to the display device 430 for presentation thereon. In some examples, the overlay device 428 may include or exhibit an HDMI input/output, with the HDMI output being connected to the display device 430. While FIG. 4B shows lines illustrating communication between the receiver device 240 and other various devices, it will be appreciated that such communication may exist, in addition or in alternate via the communication device 424 and/or the overlay device 428. In other words, any particular input to the receiver 240 as shown in FIG. 4B may additionally, or alternatively, be supplied as input to one or both of the communication device 424 and the overlay device 428.

As alluded to above, the receiver 240 may be used to provide home automation functionality, but the overlay device 428 may be used to modify a particular signal so that particular home automation information may be presented via the display device 430. Further, the home automation functionality as detailed throughout in relation to the receiver 240 may alternatively be provided by or via the overlay device 428. Using the overlay device 428 to present automation information via the display device 430 may be beneficial and/or advantageous in many respects. For instance, it is contemplated that multiple devices may provide input video to the overlay device 428. For instance, the receiver 240 may provide television programming to the overlay device 428, a DVD/Blu-Ray player may provide video to the overlay device 428, and a separate IPTV device may stream other programming to the overlay device 428.

Regardless of the source of particular video/audio, the overlay device 428 may output video and/or audio that has been modified or augmented, etc., to include home automation information and then output to the display device 430. As such, regardless of the source of video/audio, the overlay device 428 may modify the audio/video to include home automation information and, possibly, solicit user input. For instance, in some examples the overlay device 428 may have four video inputs (e.g., four HDMI inputs) and a single video output (e.g., an HDMI output). In other examples, the receiver 240 may exhibit such features or functionality. As such, a separate device, such as a Blu-ray player may be connected with a video input of the receiver 240, thus allowing the receiver 240 to overlay home automation information when content from the Blu-Ray player is being output to the display device 430.

Regardless of whether the receiver 240 is itself configured to provide home automation functionality and output home automation input for display via the display device 430 or such home automation functionality is provided via the overlay device 428, home automation information may be presented by the display device 430 while television programming is also being presented by display device 430. For instance, home automation information may be overlaid or may replace a portion of television programming, such as broadcast content, stored content, on-demand content, etc., presented via the display device 430. For example, while television programming is being presented, the display may be augmented with information related to home automation. In general, the television programming may represent broadcast programming, recorded content, on-demand content, or some other form of content. As discussed below in various embodiments, the television programming may include one or more physical conditioning video resources requested, ordered by, or recommended for a user, and the programming displayed may be augmented by various data from the user video output engine 145 based on user and location monitoring data.

An example of information related to home automation may include a security camera feed, as acquired by a camera at a front door of a residence. Such augmentation of the television programming may be performed directly by the receiver 240 (which may or may not be in communication with the communication device 424), the overlay device 428, or a combination thereof. Such augmentation may result in solid or opaque or partially transparent graphics being overlaid onto television programming (or other forms of video) output by the receiver 240 and displayed by the display device 430. Furthermore, the overlay device 428 and/or the receiver 240 may add or modify sound to television programming also or alternatively. For instance, in response to a doorbell ring, a sound may be played through the television (or connected audio system). In addition or in alternate, a graphic may be displayed. In other examples, other particular camera data (e.g., nanny camera data) and/or associated sound or motion sensors may be integrated in the system and overlaid or otherwise made available to a user. For example, detection of a crying baby from a nanny camera may trigger an on-screen alert to a user watching television.

Returning to FIG. 4B alone, the receiver 240 and/or the overlay device 428, depending on implementation-specific details, may communicate with one or more wireless devices, such as the third party device 420. The third party devices 420 may correspond to one or more user devices 160 discussed above, and represent a tablet computer, cellular phone, laptop computer, remote computer, or some other device through which a user may desire to control home automation (device) settings and view home automation information in accordance with the principles of the present disclosure. Such a device also need not necessarily be wireless, such as in a traditional desktop computer embodiment. It is contemplated that the receiver 240, communication device 424, and/or the overlay device 428 may communicate directly with the third party device 420, or may use a local wireless network, such as network 224 for instance. The third party device 420 may be remotely located and not connected with a same local wireless network as one or more of the other devices or elements of FIG. 4B.

Various home automation devices may be in communication with an event notification module of the receiver 240 and/or the overlay device 428, depending on implementation-specific details. Such home automation devices may use similar or dissimilar communication protocols. Such home automation devices may communicate with the receiver 240 directly or via the communication device 424. Such home automation devices may be controlled by a user and/or have a status viewed by a user via the display device 430 and/or third party device 420. Examples of such home automation devices are described in the following sections. It should be understood that these examples are illustrative only and not limiting, and that other types of home automation devices may be used in other examples.

One or more cameras, such as the security camera 412 may be included in the HAS 400. It is contemplated that the security camera 412 may be installed indoors, outdoors, and may provide a video and/or an audio stream that may be presented via the third party device 420 and/or display device 430. Video and/or audio from the security camera 412 may be recorded by the overlay device 428 and/or the receiver 240 continuously, in a loop as per a predefined time period, upon an event occurring, such as motion being detected by the security camera 412, and etc. For example, video and/or audio from security camera 412 may be continuously recorded such as in the form of a rolling window, thus allowing a period of time of video/audio to be reviewed by a user from before a triggering event and after the triggering event. Video/audio may be recorded on a persistent storage device local to overlay device 428 and/or the receiver 240, and/or may be recorded and stored on an external storage devices, such as a network attached storage device or back-end server memory. In some examples, video may be transmitted across a local and/or wide area network to other one or more other storage devices upon occurrence of a trigger event, for later playback. For initial setup for example, a still may be captured by the security camera 412 and stored by the receiver 240 for subsequent presentation as part of a user interface via the display device 430. In this way, an end-user can determine which camera, if multiple cameras are present or enabled, is being set up and/or later accessed. For example, a user interface may display a still image from a front door camera, which may be easily recognized by the user because it shows a scene near or adjacent a front door of a residence, to allow a user to select the front door camera for viewing as desired. As discussed below, a smell monitoring and tracking engine 145 may use image and/or video data captured from security cameras 412, in conjunction with data received via smell sensor devices 180, to identify and track particular users and objects.

Furthermore, video and, possibly, audio from the security camera 412 may be available live for viewing by a user via the overlay device 428 or the receiver 240. Such video may be presented simultaneously with television programming being presented. In some examples, video may only be presented if motion is detected by the security camera 412, otherwise video from the security camera 412 may not be presented by a particular display device presenting television programming. Also, such video (and, possibly, audio) from the security camera 408 may be recorded by the receiver 240 and/or the overlay device 428. In some examples, such video may be recorded based upon a user-configurable timer. For instance, features or functionality associated with the security camera 412 may be incorporated into an EPG that is output by the receiver 240 for display by a presentation or display device.

For instance, data as captured by the security camera 412 may be presented or may otherwise be accessible as a "channel" as part of the EPG along with other typical or conventional television programming channels. 412, a user may be permitted to select that channel associated with the security camera 408 to access data as captured by the security camera 412 for presentation via the display device 430 and/or the third party device 420, etc. The user may also be permitted to set a timer to activate the security camera 408 to record video and/or audio for a user-defined period of time on a user-defined date. Such recording may not be constrained by the rolling window mentioned above associated with a triggering event being detected. Such an implementation may be beneficial, for example, if a babysitter is going to be watching a child and the parents want to later review the babysitter's behavior in their absence. In some examples, video and/audio acquired by the security camera 412 may be backed up to a remote storage device, such as cloud-based storage hosted by an external server. Other data may also be cached to the cloud, such as configuration settings. Thus, if one or both of the receiver 240 and overlay device 428 malfunction, then a new device may be installed and the configuration data loaded onto the device from the cloud.

Further, one or more window sensors and door sensors, such as the window sensor 413 and the door sensor 414 may be integrated in to or as part of the HAS 400, and each may transmit data to the receiver 240, possibly via the communication device 424, or the overlay device 428, that indicates the status of a window or door, respectively. Such status may indicate open window or door, an ajar window or door, a closed window or door, and etc. When a status change occurs, an end-user may be notified as such via the third party device 420 and/or the display device 430, within an EPG or like interface for example. Further, a user may be able to view a status screen within an EPG or other interface to view the status one or more window sensors and/or one or more door sensors throughout the location. In some examples, the window sensor 413 and/or the door sensor 414 may have integrated "break" sensors to enable a determination as to whether glass or a hinge, or other integral component, etc., has been broken or compromised. In certain embodiments, one or both of the window sensor 413 and the door sensor 414 may be controlled via interaction with particular controls as provided within or by an EPG or like interface, and information or data as acquired by one or both of the window sensor 413 and door sensor 414 may be manipulated, consolidated, etc., as desired, and also made accessible within or by an EPG or like interface, such as a pop-up window, banner, and/or other interface or display.

Further, one or more smoke and/or CO detectors, such as detector 410, may be integrated in to or as part of the HAS 400. As such, alerts as to whether a fire (e.g., heat, smoke), CO, radon, etc., has been detected can be sent to the receiver 240, third party device 420, etc., and/or one or more emergency first responders. Accordingly, when an alert occurs, a user may be notified as such the via third party device 420 or the display device 430, within an EPG or like interface for example. Further, it is contemplated that such an interface may be utilized to disable false alarms, and that one or more sensors dispersed throughout a residence and/or integrated within the HAS 400 to detect gas leaks, radon, or various other dangerous situations. In various embodiments, a detector 410 may be controlled via interaction with particular controls as provided within or by an EPG or like interface, and information or data as acquired by the detector 410 may be manipulated, consolidated, etc., as desired, and also made accessible within or by an EPG or other interface.

Further, a pet door and/or feeder, such as pet door and/or feeder 409 may be integrated in to or as part of the HAS 400. For instance, a predefined amount of food may be dispensed at predefined times to a pet. A pet door may be locked and/or unlocked. The pet's weight or presence may trigger the locking or unlocking of the pet door. For instance, a camera located at the pet door may be used to perform image recognition of the pet or a weight sensor near the door may identify the presence of the pet and unlock the door. A user may also lock/unlock a pet door and/or dispense food for example from a "remote" location. In various embodiments, a pet door and/or feeder 409 may be controlled via interaction with particular controls as provided within or by an EPG or other interface, and data received from the pet door and/or feeder 409 may be consolidated, summarized, etc., and made accessible within or by an EPG or other interface.

Further, one or more weather sensors, such as the weather sensor 415 may be integrated in to or as part of the HAS 400, and may allow or enable the receiver 240 and/or overlay device 428 to receive, identify, and/or output various forms of environmental data, including local or non-local ambient temperature, humidity, wind speed, barometric pressure, etc. In various embodiments, weather sensors 415 may be controlled via interaction with particular controls as provided within or by an EPG or other interface, and information or data received from weather sensors 415 may be manipulated, consolidated, etc., as desired, and also made accessible within or by an EPG or other.

Further, a shade controller, such as shade controller 416, may be integrated in to or as part of the HAS 400, and may allow for control of one or more shades, such as window, door, and/or skylight shades, within a home or residence or any other location. The shade controller 416 may respond to commands received from the receiver 240 and/or overlay device 428 and may provide status updates, such as "shade up" or "shade 50% up" or "shade down" and etc. In various embodiments, shade controllers 416 may be controlled via interaction with particular controls as provided within or by an EPG or other interfaces, and data received from shade controllers 416 may be manipulated, consolidated, etc., as desired, and also made accessible within or by an EPG or other interface.

Further, one or more utility monitors, such as utility monitor 418, may be integrated in to or as part of the HAS 400, and may serve to provide the receiver 240 and/or overlay device 428 with utility data or information, such as electricity usage, gas usage, water usage, wastewater usage, irrigation usage, etc. A user may via an EPG or like interface view a status page or may receive notifications upon predefined events occurring, such as electricity usage exceeding a defined threshold within a month, or current kilowatt usage exceeding a threshold. In various embodiments, utility monitors 418 may be controlled via interaction with particular controls as provided within or by an EPG or other interface, and data received from utility monitors 418 may be manipulated, consolidated, etc., as desired, and also made accessible within or by an EPG or other interface.

Further, one or more health sensors, such as health sensor 422, may be integrated in to or as part of the HAS 400, and may permit one or more vital characteristics of a particular individual to be acquired and/or monitored, such as a heart rate for instance. In some examples, additionally or alternatively, the health sensor 422 may contain a button or other type of actuator that a user can press to request assistance. As such, the health sensor 422 may be mounted to a fixed location, such as bedside, or may be carried by a user, such as on a lanyard. Such a request may trigger a notification to be presented to other users via the display device 430 and/or the third party device 420. Additionally or if the notification is not cleared by another user within a predefined period of time, a notification may be transmitted to emergency first responders to request help. In some examples, a home automation service provider may first try contacting the user, such as via phone, to determine if an emergency is indeed occurring. Such a health sensor 422 may have additional purposes, such as for notification of another form of emergency, such as a break-in, fire, flood, theft, disaster, etc.

In some examples, health sensor 422 may be used as a medical alert pendant that can be worn or otherwise carried by an individual. It may contain a microphone and/or speaker to allow communication with other users and/or emergency first responders. The receiver 240 and/or overlay device 428 may be preprogrammed to contact a particular phone number, such as an emergency service provider, relative, medical professional, caregiver, etc., based on an actuator of the health sensor 422 being activated by a user. The user may be placed in contact with a person via the phone number and the microphone and/or speaker of the health sensor 422. Furthermore, camera data may be combined with such alerts in order to give a contacted relative more information regarding the medical situation. For example, the health sensor 422, when activated in the family room, may generate a command which is linked with security camera footage from the same room. Furthermore, in some examples, the health sensor 422 may be able to monitor vitals of a user, such as a blood pressure, temperature, heart rate, blood sugar, etc. In some examples, an event, such as a fall or exiting a structure can be detected.

Further, in response to an alert from the health sensor 422 or some other emergency or noteworthy event, parallel notifications may be sent to multiple users at approximately the same time. As such, multiple people can be made aware of the event at approximately the same time (as opposed to serial notification). Therefore, whoever the event is most pertinent to or notices the notification first can respond. Which users are notified for which type of event may be customized by a user of the receiver 240. In addition to such parallel notifications being based on data from the health sensor 422, data from other devices may trigger such parallel notifications. For instance, a mailbox open, a garage door open, an entry/exit door open during wrong time, an unauthorized control of specific lights during vacation period, a water sensor detecting a leak or flow, a temperature of room or equipment is outside of defined range, and/or motion detected at front door are examples of possible events which may trigger parallel notifications.

Additionally, a configuring user may be able to select from a list of users to notify and method of notification to enable such parallel notifications. The configuring user may prioritize which systems and people are notified, and specify that the notification may continue through the list unless acknowledged either electronically or by human interaction. For example, the user could specify that they want to be notified of any light switch operation in their home during their vacation. Notification priority could be: 1) SMS Message; 2) push notification; 3) electronic voice recorder places call to primary number; and 4) electronic voice recorder places call to spouse's number. Other examples are possible, however, it is contemplated that the second notification may never happen if the user replies to the SMS message with an acknowledgment. Or, the second notification would automatically happen if the SMS gateway cannot be contacted. In various embodiments, health sensors 422 may be controlled via interaction with particular controls as provided within or by an EPG or other interface, and data received from the health sensors 422 may be manipulated, consolidated, etc., as desired, and also made accessible within or by an EPG or other interfaces.

Further, an intercom, such as the intercom 426, may be integrated in to or as part of the HAS 400, and may permit a user in one location to communicate with a user in another location, who may be using the third party device 420, the display device 430, or some other device, such another television receiver within the structure. The intercom 426 may be integrated with the security camera 408 or may use a dedicated microphone/speaker, such as a Bluetooth® microphone. Microphones/speakers of the third party device 420, display device 430, communication device 242, overlay device 428, etc., may also or alternatively be used. A MOCA network or other appropriate type of network may be used to provide audio and/or video from the intercom 426 to the receiver 240 and/or to other television receivers and/or wireless devices in communication with the PTR 210. Here, as well as in other instances of home automation related data as acquired and served to the receiver 240 and/or overlay device 428 by particular elements of FIG. 4B, the intercom 426 may be controlled via interaction with particular controls as provided within or by an EPG or like interface, and information or data as acquired by the intercom 426 may be manipulated, consolidated, etc., as desired, and also made accessible within or by an EPG or like interface in accordance with the principles of the present disclosure.

Further, one or more light controllers, such as light controller 434, may be integrated in to or as part of the HAS 400, and may permit a light to be turned on, off, and/or dimmed by the receiver 240 or the overlay device 428, such as based on a user command received from the third party device 420 or directly via receiver 240 or overlay device 428, etc. The light controller 434 may control a single light. As such, multiple different light controllers 434 may be present within a house or residence. In some examples, a physical light switch, that opens and closes a circuit of the light, may be left in the "on" position such that light controller 434 can be used to control whether the light is on or off. The light controller 434 may be integrated into a light bulb or a circuit, such as between the light fixture and the power source, to control whether the light is on or off. An end-user, via the receiver 240 or overlay device 428, may be permitted to view a status of each instance of the light controller 434 within a location.

Since the receiver 240 or overlay device 428 may communicate using different home automation protocols, different instances of the light controller 434 within a location may use disparate or different communication protocols, but may all still be controlled by the receiver 240 or overlay device 428. In some examples, wireless light switches may be used that communicate with the receiver 240 or overlay device 428. Such switches may use a different communication protocol than any particular instance of the light controller 434. Such a difference may not affect functionality because the receiver 240 or overlay device 428 may serve as a hub for multiple disparate communication protocols and perform any necessary translation and/or bridging functions. For example, a tablet computer may transmit a command over a WiFi connection and the receiver 240 or overlay device 428 may translate the command into an appropriate Zigbee® or Zwave® command for a wireless light bulb. In some examples, the translation may occur for a group of disparate or different devices. For example, a user may decide to turn off all lights in a room and select a lighting command on a tablet computer, the overlay device 428 may then identify the lights in the room and output appropriate commands to all devices over different protocols, such as a Zigbee® wireless light bulb and a Zwave® table lamp.

Additionally, it is contemplated that the PTR 210 may permit timers and/or dimmer settings to be set for lights via the light controller 434. For instance, lights can be configured to turn on/off at various times during a day according to a schedule and/or events being detected by the HAS 400, etc. Here, as well as in other instances of home automation related data as acquired and served to the receiver 240 and/or overlay device 428 by particular elements of FIG. 4B, each particular instance of the light controller 434 may be controlled via interaction with particular controls as provided within or by an EPG or like interface, and information or data as acquired by each particular instance of the light controller 434 may be manipulated, consolidated, etc., as desired, and also made accessible within or by an EPG or like interface in accordance with the principles of the present disclosure.

Further, a thermostat, such as the thermostat 436, may be integrated in to or as part of the HAS 400, and may provide heating/cooling updates to the receiver 240 and/or overlay device 428 for display via display device 430 and/or third party device 420. Further, control of thermostat 436 may be effectuated via the receiver 240 or overlay device 428, and zone control within a structure using multiple thermostats may also be possible. Here, as well as in other instances of home automation related data as acquired and served to the receiver 240 and/or overlay device 428 by particular elements of FIG. 4B, the thermostat 436 may be controlled via interaction with particular controls as provided within or by an EPG or like interface, and information or data as acquired by the thermostat 436 may be manipulated, consolidated, etc., as desired, and also made accessible within or by an EPG or like interface in accordance with the principles of the present disclosure.

Additional appliance sensors and/or appliance controllers 438-446 also may be integrated into or included as part of the HAS 400, in order to evaluate user readiness levels for completing physical conditioning videos and/or to determine if user's have completed criteria for physical conditioning videos. In various embodiments, appliance controllers 438-446 may permit the status of the corresponding appliances to be retrieved by the receiver 240 or overlay device 428, as well as allowing commands to be sent by the receiver 240 or overlay device 428 to control operation of the appliances. Appliance controllers 438-446 may be directly integrated as part of the corresponding appliance in some cases, or may use computer software and networks, wireless communications, and the like, to connect to the corresponding appliances. Additionally or alternatively, appliance sensors and controller 438-446 may be configured to determine appliance usage data by monitoring electricity usage of one or more associated appliance (e.g., other home automation devices or circuits within a home that are monitored), or by implementing visual or audio monitoring of the appliance (e.g., using cameras 412 and microphones with video/audio analyses to detect appliance usage).

As discussed above, both personal monitoring devices associated with users, and HAS devices and systems may collect and analyze personal user data and location data in order to determine current readiness levels for users to complete certain physical conditioning videos. In FIG. 4B, appliance sensors and controllers 438-446 illustrate specific examples of appliance sensors and controllers 438-446 in a HAS 400 that may be used to collect and analyze relevant data for determining a user's readiness for completing a physical conditioning video. For example, one or more electronic scale sensors 438 may be configured to record user weight measurements and times, and to transmit that data to the receiver 240 and/or overlay device 428. Additionally, one or more water dispenser controllers 440, refrigerator appliance controllers 442, and/or other kitchen appliance controllers 444 may be configured to determine a user's recent consumption of nourishment and nutrition, and this data may be transmit to the receiver 240 and/or overlay device 428. Similarly, one or more electronic medication dispenser 446 may collect and analyze data relating to the user's use of medications and may transmit this data to the receiver 240 and/or overlay device 428. Electronic medication dispensers 446 may include external appliances such as an electronic pill dispensers, insertable or embedded medical devices such as computerized intravenous (IV) drip devices, and/or other automated medication dispensing devices.

Further, one or more home security systems, such as the home security system 411, may be integrated in to or as part of the HAS 400. In general, the home security system 411 may detect motion, when a user has armed/disarmed the home security system 411, when windows/doors are opened or broken, etc. The receiver 240 may adjust settings of the home automation devices of FIG. 4B based on home security system 411 being armed or disarmed. For example, a virtual control and alarm panel may be presented to a user via the display device 430. The functions of a wall mounted panel alarm can be integrated in the graphical user interface of the TV viewing experience such as a menu system with an underlying tree hierarchical structure. It is contemplated that the virtual control and alarm panel can appear in a full screen or PiP (Picture-in-Picture) with TV content. Alarms and event notifications may be in the form of scrolling text overlays, popups, flashing icons, etc.

Additionally, camera video and/or audio, such as from the security camera 412, can be integrated with DVR content provided by the PTR 210 with additional search, zoom, time-line capabilities. The camera's video stream can be displayed full screen, PiP with TV content, or as a tiled mosaic to display multiple camera's streams at a same time. In some examples, the display can switch between camera streams at fixed intervals. The PTR 210 may perform video scaling, adjust frame rate and transcoding on video received from the security camera 412. In addition, the receiver 240 may adaptively transcode the camera content to match an Internet connection. Here, as well as in other instances of home automation related data as acquired and served to the receiver 240 and/or overlay device 428 by particular elements of FIG. 4B, the home security system 411 may be controlled via interaction with particular controls as provided within or by an EPG or like interface, and information or data as acquired by the home security system 411 may be manipulated, consolidated, etc., as desired, and also made accessible within or by an EPG or like interface in accordance with the principles of the present disclosure.

Additional forms of appliance controllers and sensors not illustrated in FIG. 4B may also be incorporated as part of the HAS 400 in various embodiments. For instance, doorbell sensors and mailbox sensors, garage door sensors, and the like, may be implemented in the HAS 400 to detect and identify visitors at the user's location. The ability to control one or more showers, baths, faucets and/or external irrigation systems from the receiver 240 and/or the third party device 420 may also be provided in some embodiments. In some examples, a vehicle "dashcam" may upload or otherwise make video/audio available to the receiver 240 when within range of a particular residence. For instance, when a vehicle has been parked within range of a local wireless network with which the receiver 240 is connected, video and/or audio may be transmitted from the dashcam to the receiver 240 for storage and/or uploading to a remote server. Such systems or sensors or devices may be controlled via interaction with particular controls as provided within or by an EPG or like interface, and information or data as acquired by such systems or sensors or devices may be manipulated, consolidated, etc., as desired, and also made accessible within or by an EPG or like interface in certain embodiments.

Figure 5:
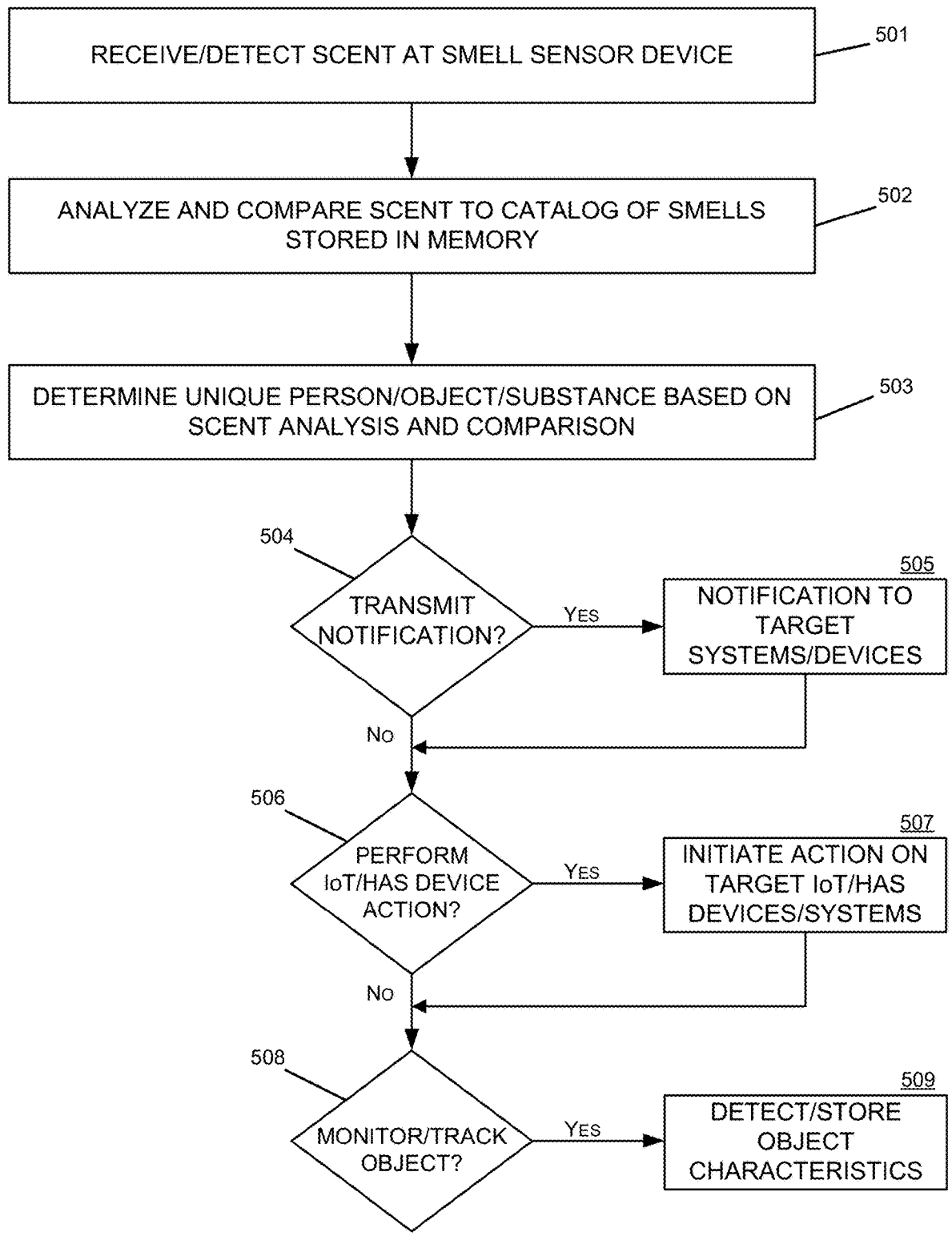
FIG. 5 is a flow diagram illustrating an example process of detecting and processing scent data at a smell sensor device, in accordance with one or more embodiments of the disclosure.

Referring now to FIG. 5, a flow diagram is shown illustrating an example process of detecting and processing scent data at a smell sensor device within a computing environment such as a media content delivery/home monitoring system 100, an IoT network 200c, and/or a home automation system (HAS) 400. As described below, the steps in this process may be performed by a smell sensor device 180, in conjunction with one or more backend servers 110, 120, 130, television receivers 140, and/or other IoT devices or home automation system devices. In other embodiments, various other devices or combinations of systems/devices in FIGS. 1-4 may be used to perform the steps described below (e.g., back-end server-based implementations, user device-based implementations, home automation system-based implementations, etc.). Additionally, it should be understood that the techniques described herein for detecting scent data at a smell sensor device 180, analyzing the scent data to identify particular persons, objects, or substances, and then performing a corresponding set of devices functions within the IoT or HAS networks, need not be limited to the specific systems and hardware implementations described above in FIGS. 1-4, but may be performed within other computing environments comprising other combinations of hardware and software components.

In step 501, a smell sensor device 180 may receive airborne scents and odors, in the form of particles and molecules carried by air currents into the smell sensors 401 of the sensor device 180. As noted above, smell sensor devices 180 may be installed in homes, shopping centers, schools, airports, public streets, or any other locations, and may be part of a home monitoring system, home automation system, and/or IoT network. Smell sensor devices 180 may operate in an always-on mode, similar to smoke alarms, security systems, carbon monoxide detectors, etc. In some embodiments, smell sensor devices 180 may have an effective range of approximately 50 feet, and thus may be positioned at approximately 50 foot intervals throughout a building or other area to be covered by the smell sensor network. Smells may be received/detected in step 501, using the smell sensors 401 within the device 180, as described above. The smell detected in step 501 may correspond to a person, an object, or any other substance. As discussed above, people as well as objects and substances may have unique smell profiles or characteristics, or smell prints, based on the reactions of the individual sensors 401 (e.g., chemical-based receptors) when they come into contact with the molecules or compounds of the received smell.

In steps 502 and 503, the smell sensor device 180 may analyze and compare the detect smell to a previously stored catalog of smell print data (step 502), and may determine the unique person, object, or substance emitting the smell based on the comparisons (step 503). As noted above, in some embodiments, a smell print catalog 407 may be stored locally within the memory of the smell sensor device 180. Additionally or alternatively, smell print catalogs/databases may be stored separately from smell sensor device 180, for example, within a separate local device (e.g., a television receiver 140, modem or router, user's smartphone, or a controller device in an IoT network), or on a central backend server (e.g., 110, 120, 130) storing a global smell print database.

These solutions also may be combined in some embodiments. For instance, the smell sensor device 180 may be preprogrammed during the manufacturing process with a number of smell prints, such as the smell print for gun powder, explosives, illegal drugs, and/or other potentially dangerous or illegal substances. Then, when the smell sensor device 180 is first installed in a home or building, it may be trained with the unique smells of the residents or other common visitors who are authorized to be present at the location. In some embodiments, the device 180 may be constantly listening for a pairing/training message from other devices, such as a user's smartphone. To train to smell sensor device 180, then user may initiate the training by sending a message from a smartphone mobile app, television receiver, or the like, which may invoke an interactive GUI application to guide the user through the steps to pair with the device, detect the unique smell print of the user (and/or other users) as well as other user characteristics. In some cases, the setup guide application may prompt the scratch their hands or arms to release skin rafts which may be detected by the smell sensors 401 and associated with the user. The guide also may prompt the user to wave or make a specific gesture that can be recognized by the depth sensors 402 of the device 180, thereby allowing the device 180 to identify the user and determine the user's size, height, and make a 3D body model of the user based on the depth sensor data. Once the smell sensor device 180 has been initialized for one or more users, with the smell print data and other characteristics (e.g., 3D body model, height, gait, posture, etc.) of each user, the smell print data and other user data may be stored within the memory 406 of the device, and/or transmitted off-device to a local controller or backend server.

Accordingly, the smell comparison in step 502 and the determination of the corresponding person/object/substance in step 503, may be performed quickly and entirely on board the smell sensor device 180 in some cases, while in other cases the smell sensor device may collect and transmit smell print data to a local controller and backend server, and then may receive a response identifying the individual, object, or substance. If the person, object, or substance has not been previously cataloged, then the determination in step 503 may be unsuccessful, and the smell sensor device 180 may transmit a request with the smell print to one or more other nearby sensors 180 and/or remote third-party data stores, to attempt to identify the new smell.

Additionally, in some embodiments, the determination of the corresponding person/object/substance in step 503 may be performed based on the combination of the detected smell print along with other sensor data received from (a) other nearby smell sensor devices 180, (b) other home monitoring/automation devices 190 (e.g., 409-446), and/or (c) IoT devices 270. For example, smell print that corresponds to a particular person but is not strong enough or unambiguous enough to be considered conclusive, may be combined with sensor data from depth sensors 402, image/video data from nearby security cameras 412, smartphone/personal device data, and/or data from any other nearby devices to confirm (or refute) the likelihood of the smell sensor determination.

Steps 504-509, described in detail below, may be performed in accordance with a set of rules and/or configuration settings that govern the particular sets of actions taken, notifications transmitted, and/or other activities performed (e.g., user monitoring/tracking) in response to the detection of particular identifiable (or unidentifiable) smell prints by particular smell sensor devices 180. In various embodiments, the rules and/or configuration settings that determine which actions are performed in steps 504-509 in response to smell detection, may be stored on the smell sensor devices 180 themselves, in local controller devices (e.g., smart phones, receivers 140, modems/routers, IoT controlling devices, etc.), and/or in one or more back-end servers (e.g., 110, 120, 130, etc.). As discussed below, the determinations in step 504, 506, and 508, which related to transmitting notifications, initiating device actions, and monitoring/tracking of users, etc., may be based on the unique smell print data detected by one or more sensor devices 180, as well various other factors including the location of the sensor device 180, the time of the smell detection, the other objects/persons detected at the same time at or near the sensor location, etc. Additionally, any or all of the determinations in step 504, 506, and 508 may be based on data from smell sensor devices 180, in combination with data from various other home monitoring/automation devices (e.g., 190 or 409-446) and/or IoT devices 270. Further, any of the same devices, such as devices within an HAS 400, IoT devices 270, and/or any other device accessible via IP networks 115 or other communication networks, may be among the devices to which notifications may be transmitted in step 505, and the devices on which actions may be initiated in step 507.

Although the examples below may refer to the smell sensor device 180 as performing the determinations and actions in steps 504-509, in other examples these steps may be performed by a separate controller device in communication with one or more smell sensor devices 180. For example, a television receiver 140, smartphone or other user device, IoT controller device, or a backend server device may be configured to receive smell data, depth data, etc. from smell sensor devices 180 and then perform the determinations and actions of steps 504-509. Further, although the method in this example first determines and transmits notifications, and then determines and performs device actions, and then determines and performs user monitoring/tracking, it should be understood that these functions may be performed in different orders, or simultaneously, in other embodiments.

In step 504, the smell sensor device 180 may determine whether one or more notifications should be transmitted, based on the smell print data identified in step 503. For example, certain sensor devices 180 may be configured to transmit notifications in response to detection of certain people (e.g., unauthorized persons at that location), objects (e.g., gun powder, explosives, or other dangerous objects), or substances (e.g., drugs, alcohol, or other prohibited substances). As noted above, the determination of whether or not to transmit notifications may be based on other data factors besides the detected smell print, such as the current location of the device 180, the current time/day, and various other contemporaneous sensor data. For instance, if gun powder is detected by a smell sensor device 180 along with a known smell print of a campus security or law enforcement officer, then the sensor 180 might be configured not to transmit a notification in this circumstance. However, if gun powder is detected without an accompanying smell print of a known security or law enforcement officer, then a notification may be transmitted.

When smell sensor device 180 determines in step 504 that one or more notifications are to be sent (504: Yes), the notifications may be transmitted to the appropriate target devices in step 505. In some cases, the notifications may be transmitted directly by the smell sensor devices 180, or may be initiated/transmitted by other devices/networks within the HAS system 400, IoT network 200c, etc. The notifications may be transmitted to different target devices based on the configuration of the smell sensor device 180, and the characteristics of the smell print and other data that triggered the notification. For example, the detection of an explosive substance in a public location may cause transmission of a notification to local law enforcement dispatch server, while the detection of drugs or alcohol at a home location may cause a notification to the smartphone of a parent or homeowner, etc.

In some cases, the notifications transmitted in step 505 may initiate interactive user sessions on the target devices. For example, a notification to a user's smartphone may invoke a mobile application session that presents the user with information about the smell print and other conditions that triggered that notification, and allows the user to provide feedback and instructions (e.g., to cancel the notification, forward the notification, invoke a function on a connected device, etc.).

In step 506, the smell sensor device 180 may determine whether any functions should be initiated on one or more connected devices. The connected devices which may be controlled in response to the detection of particular smell print data identified in step 503 (and/or other sensor data), may include any device within an HAS system 400, IoT network 200c, or any other electronic device in connection with the network on which the smell sensor device 180 is installed. When the smell sensor device 180 determines that an action is to be performed (506: Yes), either the smell sensor device 180 itself and/or other connected devices (e.g., a television receiver, network modem or router, an IoT controlling devices, a smartphones or other user device, etc.) may transmit instructions to the target device(s) to performed the desired functions in step 507. For example, in response to the detection of a dangerous object or substance in step 503, the system may initiate the closing and locking of electronic doors and windows, the activation of an alarm or security system, etc. As another example, in response to the detection in step 503 of a known user returning home, the user's profile/preferences may be retrieved and one or more home appliances or devices (e.g., lights, speakers, shades, television, thermostat, etc.) may be controlled to settings based on the user's preferences.

In step 508, the smell sensor device 180 may determine whether any the smell data determined in step 503 corresponds to a person whose activities should be monitored/tracked while in range of the smell sensor device 180. As noted above, the detection of a unique individual using the smell sensor device 180 may include smell print detection and comparison, as well as detection and comparison of the user's body shape/3D profile using depth sensors 402. Data from additional connected sensors may be used in the determination of the unique person as well, including image data, audio data, communications with personal user devices, etc. In some embodiments, a smell sensor device 180 may be configured to monitor and track all persons within range of the device 180, while in other cases a smell sensor device 180 may be configured to monitor/track only a predetermined fixed number of users (e.g., family members, employees, authorized users at the location). Alternatively, a smell sensor device 180 may be configured to monitor and track only unidentified persons (e.g., persons without an existing smell print profile in the database). If the smell sensor device 180 determines that an individual identified in step 503 is to be monitored/tracked (508: Yes), then the sensor device 180 may initiate one or more processes to track and monitor the individual, including generation and storage of monitoring data, transmission of data to back-end servers, and/or executing handoff processes between other sensor devices 180. These processes relating to user monitoring and track are described below in more detail in reference to FIG. 6.

Figure 6:
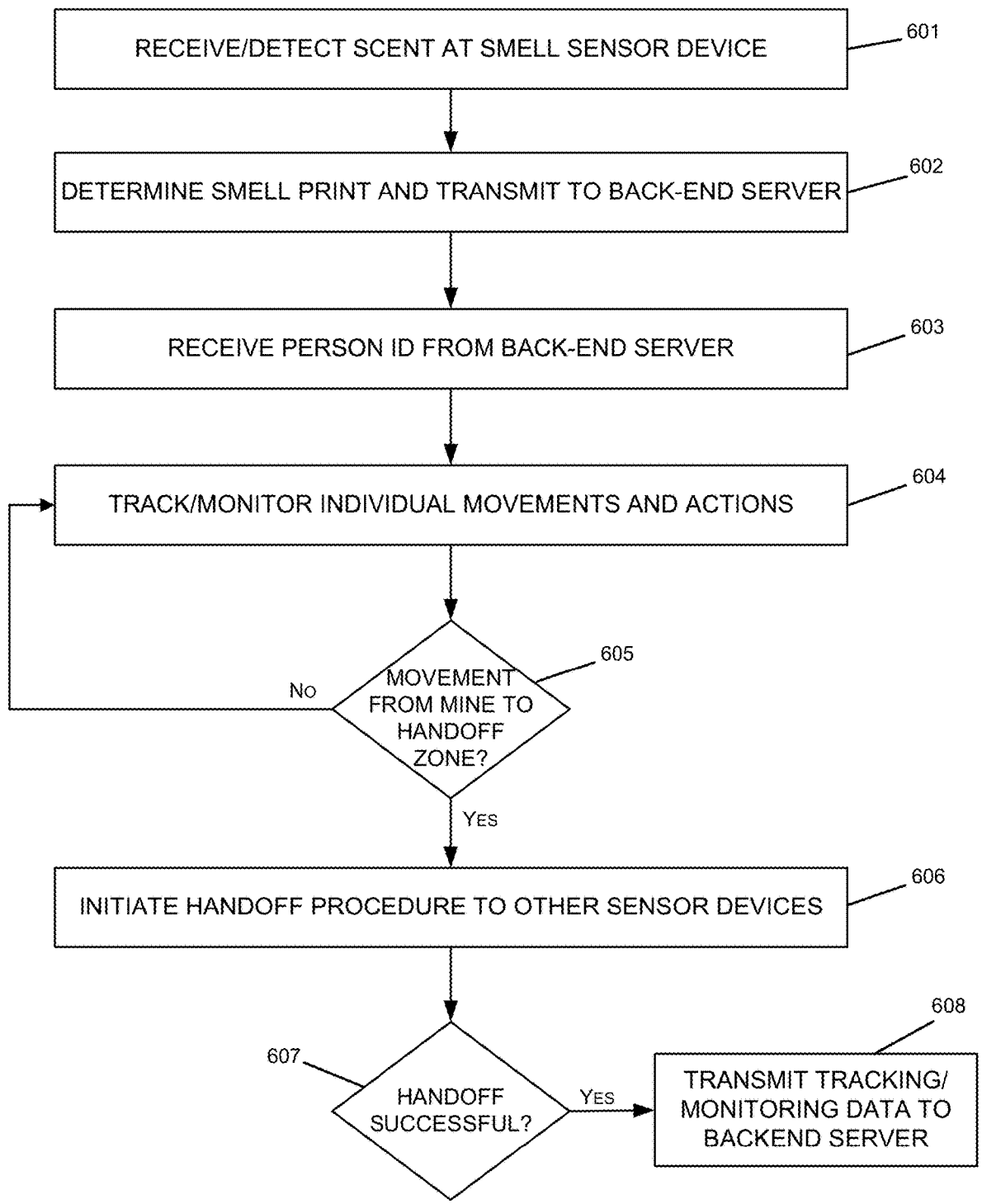
FIG. 6 is a flow diagram illustrating an example process of tracking and monitoring user movement and activities, using one or more smell sensor devices, in accordance with one or more embodiments of the disclosure.

Referring now to FIG. 6, a flow diagram is shown illustrating an example process of tracking and monitoring a particular user, using a smell sensor device 180 or network of devices 180. As described below, the steps in this process may be performed by one or more individual smell sensor devices 180, in communication with other nearby sensor devices 180-190, and/or in communication with a backend server 110, 120, or 130, television receiver 140, and/or other IoT devices or home automation system devices. In other embodiments, various other devices or combinations of systems/devices in FIGS. 1-4 may be used to perform the steps described below (e.g., backend server-based implementations, user device-based implementations, home automation system-based implementations, etc.). Additionally, it should be understood that the techniques described herein for detecting scent data at smell sensor devices 180, identifying particular persons based on the unique smell print data, and then tracking and monitoring the person's activities with the network of smell sensor devices 180, need not be limited to the specific systems and hardware implementations described above in FIGS. 1-4, but may be performed within other computing environments comprising other combinations of hardware and software components.

In step 601, a smell sensor device 180 may receive and detect airborne scents and odors via the smell sensors 401 of the device 180. Thus, step 601 may be similar or identical to step 501, described above. In this example, the smell detected in step 601 may correspond to one or more persons, which may have unique smell profiles or characteristics (also referred to as smell prints), that can be detected and recorded based on the reactions of the individual sensors 401 (e.g., chemical-based receptors) when they come into contact with the molecules or compounds of the received smell.

In step 602, the smell sensor device 180 may use the smell/odor data detected in step 601, to generate a smell print and transmit a hash of the smell print (or the smell print itself) to a backend server (e.g., 110, 120, or 130) containing a person-smell print database. The smell print may be generated by encoding the received smell data/smell characteristics of the individual into predetermined encoding format, which then may be input to a cryptographic hashing function to generate a hash value for transmission to the backend server. After receiving the smell print hash from the smell sensor device 180, the backend server (e.g., 110) may analyze and compare the smell print hash to a data store of individual smell print profiles. After identifying a matching smell print profile, the backend server 110 may transmit the corresponding person identifier of the matching person back to the smell sensor device 180, in step 603.

In some embodiments, steps 602-603 may include transmitting additional data to along with the smell print hash (or other small print data) detected in step 601. For example, the smell sensor device 180 may determine person size/shape data using its depth sensors 402 and/or additional object distance/location sensors, and may transmit the size/shape data for one or more persons to backend server along with the smell print data. In some cases, a smell sensor device 180 may generate a transmit a 3D body model of one or more persons within range of the depth sensors 402 and may transmit the 3D body model data to the backend server 110 only with one or more smell prints. In such cases, 3D body models and/or other person size/shape data may be stored in a related backend database, so that the backend server 110 may use the combination of the smell print and 3D body model data to determine the matching person with greater confidence and/or to resolve any potential ambiguities. For instance, if two people walking together enter the range of a smell sensor device 180, the device 180 may collect and transmit two separate smell prints (and/or two separate 3D body models) to the backend server 110. The backend server 110 may identify the two individuals based on the smell print data (and/or 3D body models), and then may transmit back both matching person identifiers along with associated 3D body model data retrieved from the database for both persons. The sensor device 180 may then use the received 3D body model data to determine which person identifier matches which individual within its sensor range. This allows the smell sensor device 180 to determine definitively for which person it is tracking and monitoring, which also prevents potential errors in handoff and data collection/backup processes, as discussed below.

In step 604, the smell sensor device 180 may begin to track and monitor the movements and actions of the person (s) identified in step 603. Although step 604 is shown following step 603 in this example, in some cases the smell sensor device 180 may commence tracking/monitoring of a person even before the persons can be positively identified. In some embodiments, a smell sensor device 180 may be configured to track/monitor all persons that enter within its sensing range, while in other cases it may be configured to track only certain predetermined users (e.g., family members).

During the monitoring and tracking process, the smell sensor device 180 may use the depth and location sensors to start capturing various data including, for example, user step data, body posture (e.g., sleeping, sitting, etc.), user speed, and/or user location data. The user monitoring and tracking data may be collected continuously or periodically by the smell sensor device 180 for each individual user within the range of the device 180. The resulting monitoring/tracking data may be collected and stored locally within the memory 406/407 of the sensor device. Referring briefly to FIG. 7, an example data entry is shown for a tracking/monitoring process executed by a smell sensor device 180 for a particular person.

Figure 8:
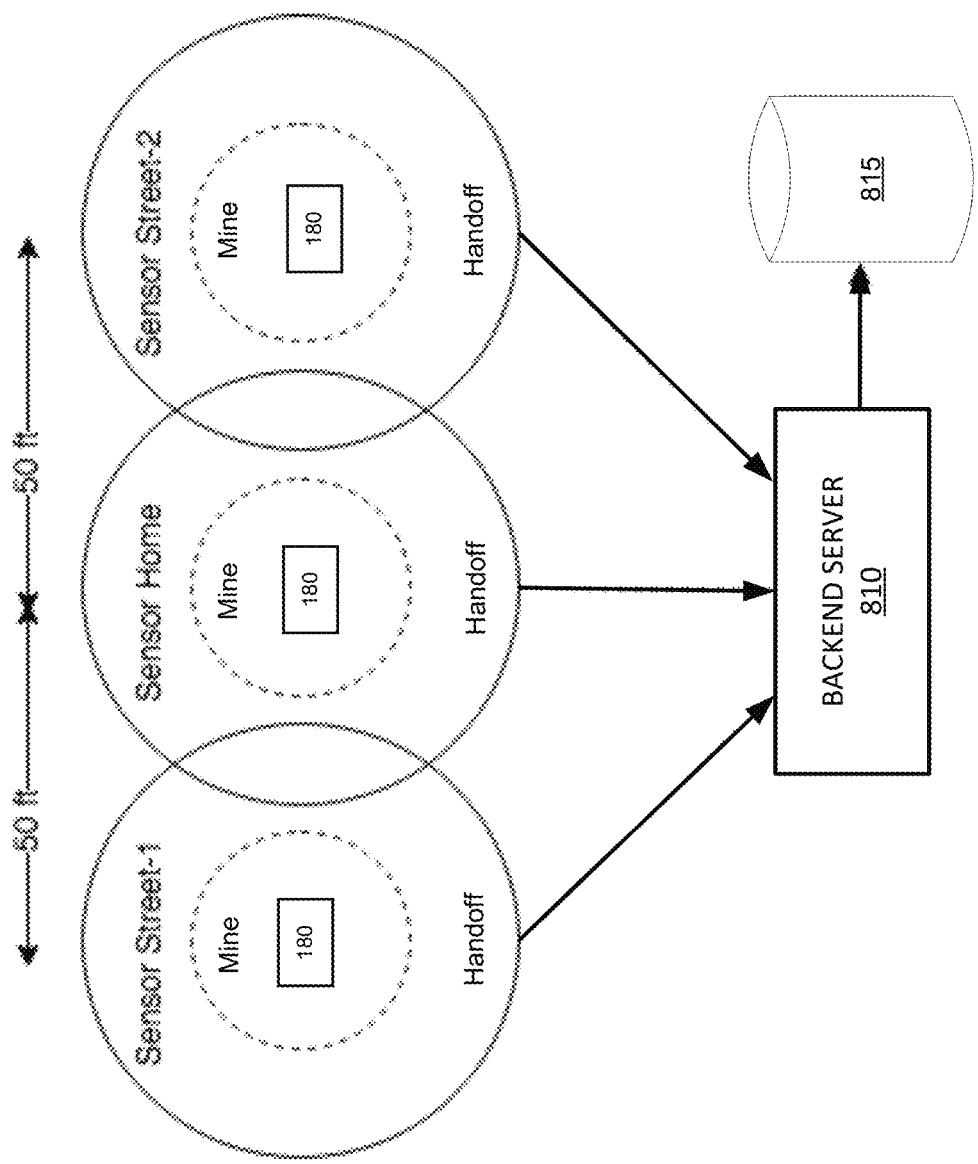
FIG. 8 is example system diagram illustrating a layout and handoff procedure between multiple smell sensor devices, in accordance with one or more embodiments of the disclosure.

As noted above, smell sensors 401 may have limited effective ranges in some cases. For instance, certain smell sensors 401 are limited to a range of 50 feet. Therefore, it may be preferred to install a different smell sensor device 180 every 50 feet to ensure complete coverage of the desired area (e.g., home, school, public square, etc.). Because the range of the smell sensors 401 may dictate generally circular zones of coverage, different smell sensor devices 180 are likely to have at least overlapping sensor coverage areas. For example, referring briefly to FIG. 8, an example is shown of a coverage map including three circular zones for three separate smell sensor devices 180. In this example, the innermost zones labeled "Mine" correspond to areas where it is assumed that this smell sensor device 180 is likely the only device capable of smelling a person. In contrast, the outer "Handoff" zones correspond to areas where the smell strength detected by the sensor 401 may be low, and the device 180 is near the outer range of being able to detect the person by smell. As shown in this example, "Handoff" zones of different sensor devices 180 may overlap, which may be used to facilitate user monitoring/tracking handoff processes. An example of a handoff process between two smell sensor devices 180 is described below in steps 605-608.

In step 605, the smell sensor device 180 determines whether a person being monitored has moved from the inner "Mine" zone of the sensor's range to the outer "Handoff" zone. When device 180 detects that a person has moved from the Mine zone of the device to the Handoff zone (605: Yes), then in step 606 it may initiate the handoff procedure to by communicating with one or more other nearby sensor devices 180. For example, when a smell sensor device 180 detects that a person has moved from its Mine zone to its Handoff zone, it may broadcast a handoff message (e.g., a radio message or other short-range wireless communication) locally to notify nearby smell sensor devices 180 that a person is moving to another device territory. In some embodiments, this handoff message may contain (i) the device identifier of the transmitting device, (ii) the person identifier (e.g., received from the backend server in step 603), and (iii) the current location of the person. The smell sensor devices 180 may determine person's current location using its own GPS/location system 404, along with depth sensors 402, range/distance sensor 403 and/or other sensors within the device 180 (e.g., gyroscope, compass, etc.). Then, when a second smell sensor device 180-2 (e.g., Sensor Street-1 or -2), receives the handoff message broadcasted from the first smell sensor device 180 identifying a person whose location is within its territory, then the second smell sensor device 180-2 may respond with a receipt message. The receipt message in the handoff process may contain (i) the device identifier, (ii) the person identifier, and (iii) the current location of the person. Then, the original smell sensor device 180-1 may send a final acknowledgment message to confirm the hand-off to the second device 180-2. In some cases, the final acknowledgment message may contain (i) the identifier of the first smell sensor device 180-1, (ii) the identifier of the second smell sensor device 180-2, and (iii) a current timestamp.

In step 607, after the above messages have been sent and acknowledged, thus confirming a successful handoff from one smell sensor device 180-1 to another 180-2, then in step 608, the first smell sensor device 180-1 may transmit any monitoring/tracking information captured for the person, to one or more backend systems (e.g., 110). As noted above, in some cases the monitoring/tracking data collected by a smell sensor device 180 may be stored on the device itself, or alternatively within a local receiver 140, modem/router, or other controlling device. Thus, in various embodiments, the determination in step 607 and data transmission in step 608 may be performed directly by the first smell sensor device 180-1, by a software component 145 within the local television receiver/controller 140, by the user's smartphone or other computing device, or by a separate HAS controller or IoT controller device operating at the location.

At or around the same time, the new smell sensor device 180-2 may contact the backend server 110 using the person identifier to retrieve the smell print of the person (and/or 3D body model or other person size/shape data). Using the smell print (and/or 3D body model or other person size/shape data), the new smell sensor device 180-2 may immediately locate the person and begin to capture monitoring/tracking data for the person.

The backend server 110 may, either periodically or in response to a particular request, compile and aggregate together the monitoring/tracking data for the individual, which may consist of data gathered by any number of separately operating smell sensor devices 180. The aggregated data may include, for example, a calculation of the total number of steps taken by the person, the average walking/running speed of the person, the person's body posture over time, and/or a tracking map of the locations visited by the person (e.g., rooms, stores, streets, etc.) and how long the person stayed at each location. In embodiments where a network of devices 180 are installed in a large area (e.g., shopping mall, school campus, public streets, etc.) the aggregated data may have been gathered by dozens or even hundreds of devices 180.

Figure 9:
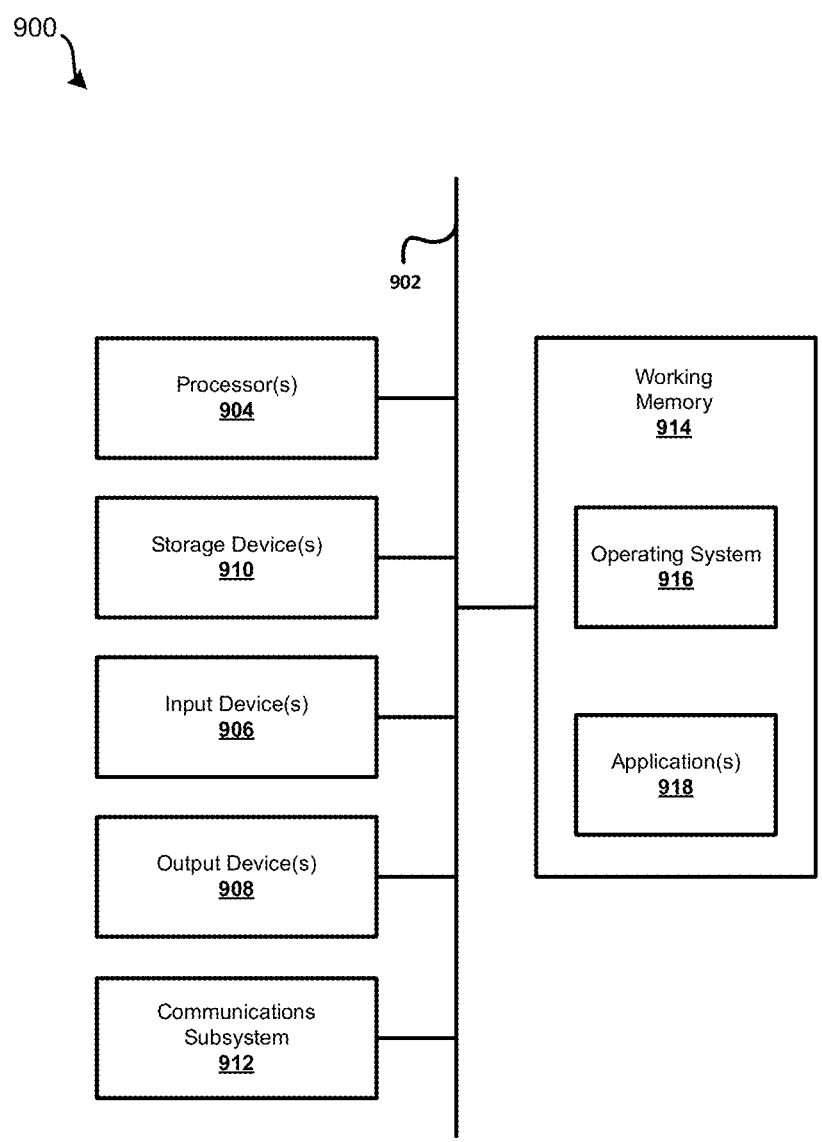
FIG. 9 is a block diagram illustrating an example computing system upon which various features of the present disclosure may be implemented.

Referring now to FIG. 9, an example is shown of a computer system or device 900 in accordance with the disclosure. Examples of computer systems or devices 900 may include systems, controllers, servers, monitors, sensors, or the like, an enterprise server, blade server, desktop computer, laptop computer, tablet computer, personal data assistant, smartphone, gaming console, set-top box, television receiver, "smart" home automation-related sensor or device or system or controller or monitor or detector, and/or any other type of machine configured for performing calculations. Any particular one of the previously-described computing devices may be wholly or at least partially configured to exhibit features similar to the computer system 900, such as any of the respective elements or components of FIGS. 1-4. In this manner, any of one or more of the respective elements of those figures may be configured and/or arranged, wholly or at least partially, for detecting and identifying particular individuals, objects, and substances using a network of smell sensor devices, as well as monitoring and tracking user movements and activities based on the smell sensor data, as discussed above. Still further, any of one or more of the respective elements of FIGS. 1-4 may be configured and/or arranged to include computer-readable instructions that, when executed, instantiate and implement various functionality described herein (e.g., one or more user output engines, devices, or services 145).

The computer device 900 is shown comprising hardware elements that may be electrically coupled via a bus 902 (or may otherwise be in communication, as appropriate). The hardware elements may include a processing unit with one or more processors 904, including without limitation one or more general-purpose processors and/or one or more special-purpose processors (such as digital signal processing chips, graphics acceleration processors, and/or the like); one or more input devices 906, which may include without limitation a remote control, a mouse, a keyboard, and/or the like; and one or more output devices 908, which may include without limitation a presentation device (e.g., television), a printer, and/or the like.

The computer system 900 may further include (and/or be in communication with) one or more non-transitory storage devices 910, which may comprise, without limitation, local and/or network accessible storage, and/or may include, without limitation, a disk drive, a drive array, an optical storage device, a solid-state storage device, such as a random access memory, and/or a read-only memory, which may be programmable, flash-updateable, and/or the like. Such storage devices may be configured to implement any appropriate data stores, including without limitation, various file systems, database structures, and/or the like.

The computer device 900 might also include a communications subsystem 912, which may include without limitation a modem, a network card (wireless and/or wired), an infrared communication device, a wireless communication device and/or a chipset such as a Bluetooth™ device, 802.11 device, WiFi device, WiMax device, cellular communication facilities such as GSM (Global System for Mobile Communications), W-CDMA (Wideband Code Division Multiple Access), LTE (Long Term Evolution), etc., and/or the like. The communications subsystem 912 may permit data to be exchanged with a network (such as the network described below, to name one example), other computer systems, and/or any other devices described herein. In many examples, the computer system 900 will further comprise a working memory 914, which may include a random access memory and/or a read-only memory device, as described above.

The computer device 900 also may comprise software elements, shown as being currently located within the working memory 914, including an operating system 916, device drivers, executable libraries, and/or other code, such as one or more application programs 918, which may comprise computer programs provided by various examples, and/or may be designed to implement methods, and/or configure systems, provided by other examples, as described herein. By way of example, one or more procedures described with respect to the method(s) discussed above, and/or system components might be implemented as code and/or instructions executable by a computer (and/or a processor within a computer); in an aspect, then, such code and/or instructions may be used to configure and/or adapt a general purpose computer (or other device) to perform one or more operations in accordance with the described methods.

A set of these instructions and/or code might be stored on a non-transitory computer-readable storage medium, such as the storage device(s) 910 described above. In some cases, the storage medium might be incorporated within a computer system, such as computer system 900. In other examples, the storage medium might be separate from a computer system (e.g., a removable medium, such as flash memory), and/or provided in an installation package, such that the storage medium may be used to program, configure, and/or adapt a general purpose computer with the instructions/code stored thereon. These instructions might take the form of executable code, which is executable by the computer device 900 and/or might take the form of source and/or installable code, which, upon compilation and/or installation on the computer system 900 (e.g., using any of a variety of generally available compilers, installation programs, compression/decompression utilities, etc.), then takes the form of executable code.

It will be apparent that substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed.

As mentioned above, in one aspect, some examples may employ a computer system (such as the computer device 900) to perform methods in accordance with various examples of the disclosure. According to a set of examples, some or all of the procedures of such methods are performed by the computer system 900 in response to processor 904 executing one or more sequences of one or more instructions (which might be incorporated into the operating system 916 and/or other code, such as an application program 918) contained in the working memory 914. Such instructions may be read into the working memory 914 from another computer-readable medium, such as one or more of the storage device(s) 910. Merely by way of example, execution of the sequences of instructions contained in the working memory 914 may cause the processor(s) 904 to perform one or more procedures of the methods described herein.

The terms "machine-readable medium" and "computer-readable medium," as used herein, may refer to any non-transitory medium that participates in providing data that causes a machine to operate in a specific fashion. In an example implemented using the computer device 900, various computer-readable media might be involved in providing instructions/code to processor(s) 904 for execution and/or might be used to store and/or carry such instructions/code. In many implementations, a computer-readable medium is a physical and/or tangible storage medium. Such a medium may take the form of a non-volatile media or volatile media. Non-volatile media may include, for example, optical and/or magnetic disks, such as the storage device(s) 910. Volatile media may include, without limitation, dynamic memory, such as the working memory 914.

Example forms of physical and/or tangible computer-readable media may include a floppy disk, a flexible disk, hard disk, magnetic tape, or any other magnetic medium, a compact disc, any other optical medium, ROM (Read Only Memory), RAM (Random Access Memory), and etc., any other memory chip or cartridge, or any other medium from which a computer may read instructions and/or code. Various forms of computer-readable media may be involved in carrying one or more sequences of one or more instructions to the processor(s) 904 for execution. By way of example, the instructions may initially be carried on a magnetic disk and/or optical disc of a remote computer. A remote computer might load the instructions into its dynamic memory and send the instructions as signals over a transmission medium to be received and/or executed by the computer system 900.

The communications subsystem 912 (and/or components thereof) generally will receive signals, and the bus 902 then might carry the signals (and/or the data, instructions, etc. carried by the signals) to the working memory 914, from which the processor(s) 904 retrieves and executes the instructions. The instructions received by the working memory 914 may optionally be stored on a non-transitory storage device 910 either before or after execution by the processor(s) 904. It should further be understood that the components of computer device 900 can be distributed across a network. For example, some processing may be performed in one location using a first processor while other processing may be performed by another processor remote from the first processor. Other components of computer system 900 may be similarly distributed. As such, computer device 900 may be interpreted as a distributed computing system that performs processing in multiple locations. In some instances, computer system 900 may be interpreted as a single computing device, such as a distinct laptop, desktop computer, or the like, depending on the context.

The methods, systems, and devices discussed above are examples. Various configurations may omit, substitute, or add various method steps or procedures, or system components as appropriate. For instance, in alternative configurations, the methods may be performed in an order different from that described, and/or various stages or steps or modules may be added, omitted, and/or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those of skill with an enabling description for implementing described techniques. Various changes may be made in the function and arrangement of elements without departing from the spirit or scope of the disclosure.

Also, configurations may be described as a process which is depicted as a flow diagram or block diagram. Although each may describe the operations as a sequential process, many of the operations may be performed in parallel or concurrently. In addition, the order of the operations may be rearranged. A process may have additional steps not included in the figure. Furthermore, examples of the methods may be implemented by hardware, software, firmware, middleware, microcode, hardware description languages, or any combination thereof. When implemented in software, firmware, middleware, or microcode, the program code or code segments to perform the necessary tasks may be stored in a non-transitory computer-readable medium such as a storage medium. Processors may perform the described tasks.

Furthermore, the examples described herein may be implemented as logical operations in a computing device in a networked computing system environment. The logical operations may be implemented as: (i) a sequence of computer implemented instructions, steps, or program modules running on a computing device; and (ii) interconnected logic or hardware modules running within a computing device.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A smell sensor device, comprising:
one or more smell detectors comprising chemical-based receptor sensors, the one or more smell detectors configured to capture and analyze detect airborne scent data in the proximity of the smell sensor device;
one or more depth sensors configured to detect characteristics of physical objects in the proximity of the smell sensor device;
a wireless network interface;
a processing unit comprising one or more processors; and
memory coupled with and readable by the processing unit and storing therein a set of computer-executable instructions which, when executed by the processing unit, causes the smell sensor device to:
detect scent data in the proximity of the smell sensor device, using the one or more smell detectors;
detect one or more physical objects that are within a detection range of the one or more depth sensors at a time concurrent with the detection of the scent data;
identify a particular object in the proximity of the smell sensor device, by comparing the detected scent data and one or more characteristics of the one or more detected physical objects, in a database storing data representing a plurality of different objects; and
initiate a particular set of functionalities on the smell sensor device, in response to the identification of the particular object.

2. The smell sensor device of claim 1, wherein the database stores data representing scent data and physical object characteristic data for a plurality of unique individuals and objects, and wherein the data is stored in the memory of the smell sensor device.

3. The smell sensor device of claim 1, further comprising:
a global positioning system (GPS) receiver, wherein the smell sensor device is further configured to:
determine a location associated with the particular object identified by the smell sensor device, using the GPS receiver; and
transmit data identifying the particular object identified by the smell sensor device, and the determined location associated with the particular object, to a recipient system.

4. The smell sensor device of claim 1, wherein initiating the particular set of functionalities on the smell sensor device comprises:
determining an automated device function to performed, in response to the identification of the particular object;
selecting a target device to perform the automated device function, wherein the target device is at least one of an Internet-of-Things (IoT) device, or a device within a home automation system (HAS); and
transmitting instructions from the smell sensor device to the target device to perform the automated device function.

5. The smell sensor device of claim 1, wherein initiating the particular set of functionalities on the smell sensor device comprises:
determining a recipient device to notify, wherein the recipient device is selected from a plurality of devices based on the particular object identified;
transmitting a notification to the determined recipient device, the notification including data identifying the particular object.

6. The smell sensor device of claim 1, wherein initiating the particular set of functionalities on the smell sensor device comprises:
monitoring the particular object within the detection range of the one or more depth sensors of the smell sensor device;
during the monitoring of the particular object, detecting a movement of the particular object from an inner zone within the detection range of the depth sensors to a handoff zone within the detection range of the depth sensors;
in response to the detected movement of the particular object from the inner zone to the handoff zone, transmitting a request to a second smell sensor device associated with the handoff zone, to initiate a procedure to handoff monitoring of the particular object to the second smell sensor device.

7. The smell sensor device of claim 6, wherein initiating the particular set of functionalities on the smell sensor device further comprises:
in response to a determination that the procedure to handoff monitoring of the particular object to the second smell sensor device was successful: (a) stopping the monitoring of the particular object by the depth sensors of the smell sensor device, and (b) transmitting a set of monitoring data collected during the monitoring of the particular object, to a backend server.

8. A method of physical object monitoring using a smell sensor device, the method comprising:
detecting, by a smell sensor device, scent data in the proximity of the smell sensor device, using one or more smell detectors within the smell sensor device;
detecting, by the smell sensor device, one or more physical objects that are within a detection range of one or more depth sensors within the smell sensor device, at a time concurrent with the detection of the scent data;
identifying, by the smell sensor device, a particular object in the proximity of the smell sensor device, by comparing the detected scent data and one or more characteristics of the one or more detected physical objects, in a database storing data representing a plurality of different objects; and
initiating, by the smell sensor device, a particular set of functionalities on the smell sensor device, in response to the identification of the particular object.

9. The method of physical object monitoring of claim 8, wherein the database stores data representing scent data and physical object characteristic data for a plurality of unique individuals and objects, and wherein the data is stored in a memory of the smell sensor device.

10. The method of physical object monitoring of claim 8, further comprising:
determining a location associated with the particular object identified by the smell sensor device, using a global positioning system (GPS) receiver of the smell sensor device; and transmitting data identifying the particular object identified by the smell sensor device, and the determined location associated with the particular object, to a recipient system.

11. The method of physical object monitoring of claim 8, wherein initiating the particular set of functionalities on the smell sensor device comprises:
determining an automated device function to performed, in response to the identification of the particular object;
selecting a target device to perform the automated device function, wherein the target device is at least one of an Internet-of-Things (IoT) device, or a device within a home automation system (HAS); and
transmitting instructions from the smell sensor device to the target device to perform the automated device function.

12. The method of physical object monitoring of claim 8, wherein initiating the particular set of functionalities on the smell sensor device comprises:
determining a recipient device to notify, wherein the recipient device is selected from a plurality of devices based on the particular object identified;
transmitting a notification to the determined recipient device, the notification including data identifying the particular object.

13. The method of physical object monitoring of claim 8, wherein initiating the particular set of functionalities on the smell sensor device comprises:
monitoring the particular object within the detection range of the one or more depth sensors of the smell sensor device;
during the monitoring of the particular object, detecting a movement of the particular object from an inner zone within the detection range of the depth sensors to a handoff zone within the detection range of the depth sensors;
in response to the detected movement of the particular object from the inner zone to the handoff zone, transmit a request to a second smell sensor device associated with the handoff zone, to initiate a procedure to handoff monitoring of the particular object to the second smell sensor device.

14. The method of physical object monitoring of claim 13, wherein initiating the particular set of functionalities on the smell sensor device further comprises:
in response to a determination that the procedure to handoff monitoring of the particular object to the second smell sensor device was successful: (a) stopping the monitoring of the particular object by the depth sensors of the smell sensor device, and (b) transmitting a set of monitoring data collected during the monitoring of the particular object, to a backend server.

15. A non-transitory computer-readable memory comprising a set of instructions stored therein which, when executed by a processing unit of a smell sensor device, causes the processing unit to:
detect scent data in the proximity of the smell sensor device, using one or more smell detectors within the smell sensor device;
detect one or more physical objects that are within a detection range of one or more depth sensors within the smell sensor device, at a time concurrent with the detection of the scent data;
identify a particular object in the proximity of the smell sensor device, by comparing the detected scent data and one or more characteristics of the one or more detected physical objects, in a database storing data representing a plurality of different objects; and
initiate a particular set of functionalities on the smell sensor device, in response to the identification of the particular object.

16. The non-transitory computer-readable memory of claim 15, comprising additional instructions which, when executed by the processing unit of the smell sensor device, cause the processing unit to:
determine a location associated with the particular object identified by the smell sensor device, using a global positioning system (GPS) receiver of the smell sensor device; and
transmit data identifying the particular object identified by the smell sensor device, and the determined location associated with the particular object, to a recipient system.

17. The non-transitory computer-readable memory of claim 15, wherein initiating the particular set of functionalities on the smell sensor device comprises:
determining an automated device function to performed, in response to the identification of the particular object;
selecting a target device to perform the automated device function, wherein the target device is at least one of an Internet-of-Things (IoT) device, or a device within a home automation system (HAS); and
transmitting instructions from the smell sensor device to the target device to perform the automated device function.

18. The non-transitory computer-readable memory of claim 15, wherein initiating the particular set of functionalities on the smell sensor device comprises:
determining a recipient device to notify, wherein the recipient device is selected from a plurality of devices based on the particular object identified;
transmitting a notification to the determined recipient device, the notification including data identifying the particular object.

19. The non-transitory computer-readable memory of claim 15, wherein initiating the particular set of functionalities on the smell sensor device comprises:
monitoring the particular object within the detection range of the one or more depth sensors of the smell sensor device;
during the monitoring of the particular object, detecting a movement of the particular object from an inner zone within the detection range of the depth sensors to a handoff zone within the detection range of the depth sensors;
in response to the detected movement of the particular object from the inner zone to the handoff zone, transmit a request to a second smell sensor device associated with the handoff zone, to initiate a procedure to handoff monitoring of the particular object to the second smell sensor device.

20. The non-transitory computer-readable memory of claim 19, wherein initiating the particular set of functionalities on the smell sensor device further comprises:
in response to a determination that the procedure to handoff monitoring of the particular object to the second smell sensor device was successful: (a) stopping the monitoring of the particular object by the depth sensors of the smell sensor device, and (b) transmitting a set of monitoring data collected during the monitoring of the particular object, to a backend server.

* * * * *